US009855060B2

(12) United States Patent
Ardel et al.

(10) Patent No.: US 9,855,060 B2
(45) Date of Patent: Jan. 2, 2018

(54) DEVICE FOR MODIFYING THE OPERATION OF SURGICAL BONE TOOLS AND/OR METHODS THEREOF

(71) Applicant: OrthoDrill Medical Ltd., Binyamina (IL)

(72) Inventors: Ehud Ardel, Givat Ada (IL); Shlomo David, Binyamina (IL)

(73) Assignee: OrthoDrill Medical Ltd., Binyamina (IL)

( * ) Notice: Subject to any disclaimer, the term of this patent is extended or adjusted under 35 U.S.C. 154(b) by 0 days.

(21) Appl. No.: 15/177,693

(22) Filed: Jun. 9, 2016

(65) Prior Publication Data
US 2016/0361069 A1    Dec. 15, 2016

Related U.S. Application Data

(60) Provisional application No. 62/173,365, filed on Jun. 10, 2015.

(51) Int. Cl.
*A61B 17/16* (2006.01)
*A61B 17/00* (2006.01)
(Continued)

(52) U.S. Cl.
CPC ........ *A61B 17/1626* (2013.01); *A61B 17/162* (2013.01); *A61B 17/1617* (2013.01);
(Continued)

(58) Field of Classification Search
CPC .............. A61B 17/162; A61B 17/1624; A61B 17/1628; A61B 17/1626
(Continued)

(56) References Cited

U.S. PATENT DOCUMENTS 4,600,006 A    7/1986 Baker
6,033,409 A    3/2000 Allotta
(Continued)

FOREIGN PATENT DOCUMENTS

CN    101530341    9/2009
CN    102370509    3/2012
(Continued)

OTHER PUBLICATIONS

International Search Report and the Written Opinion dated Sep. 19, 2016 From the International Searching Authority Re. Application No. PCT/IL2016/050613.
(Continued)

*Primary Examiner* — Samuel Hanna

(57) ABSTRACT

Provided herein is an adaptor for modifying the operation of a surgical bone-tool, comprising: a housing having a distal end and a proximal end coupled between a chuck and an operating bit of said tool, such that force generated by a motor of the tool is delivered to the operating bit through the adaptor; a clutch, contained in the housing, having an engaged and a disengaged configurations, respectively interconnecting and disconnecting the chuck to the operating bit; the clutch automatically disengages in response to an electric current, causing a cutoff of the force delivery; wherein the housing comprises a proximal fastener, sized and shaped to connect with the operating bit and a distal fastener, sized and shaped to connect with the chuck.

14 Claims, 16 Drawing Sheets

(51) Int. Cl.
*A61B 17/15* (2006.01)
*A61B 90/57* (2016.01)
*A61B 90/53* (2016.01)
*A61B 90/60* (2016.01)
*A61B 34/20* (2016.01)

(52) U.S. Cl.
CPC ........... *A61B 17/15* (2013.01); *A61B 17/1622* (2013.01); *A61B 17/1628* (2013.01); *A61B 90/53* (2016.02); *A61B 90/60* (2016.02); *A61B 2017/00026* (2013.01); *A61B 2017/00039* (2013.01); *A61B 2017/00084* (2013.01); *A61B 2017/00106* (2013.01); *A61B 2017/00119* (2013.01); *A61B 2017/00123* (2013.01); *A61B 2017/00128* (2013.01); *A61B 2017/00199* (2013.01); *A61B 2017/00694* (2013.01); *A61B 2034/2048* (2016.02); *A61B 2090/571* (2016.02)

(58) Field of Classification Search
USPC .................................................. 318/432–433
See application file for complete search history.

(56) References Cited

U.S. PATENT DOCUMENTS

| | | | |
|---|---|---|---|
| 6,336,931 | B1 | 1/2002 | Hsu et al. |
| 7,638,958 | B2 | 12/2009 | Philipp et al. |
| 7,771,143 | B2 | 8/2010 | Bharadwaj et al. |
| 8,463,421 | B2 | 6/2013 | Brett et al. |
| 8,511,945 | B2 | 8/2013 | Apkarian et al. |
| 8,821,493 | B2 | 9/2014 | Anderson |
| 8,926,614 | B2 | 1/2015 | Hsieh |
| 2002/0120197 | A1 | 8/2002 | Kleffner et al. |
| 2003/0023167 | A1 | 1/2003 | Azzam et al. |
| 2005/0116673 | A1* | 6/2005 | Carl .................. A61B 17/1626 318/432 |
| 2005/0131415 | A1 | 6/2005 | Hearn et al. |
| 2009/0024129 | A1 | 1/2009 | Gordon et al. |
| 2009/0228011 | A1 | 9/2009 | Agbodoe et al. |
| 2009/0299439 | A1* | 12/2009 | Mire ................. A61B 17/1626 607/60 |
| 2010/0143861 | A1 | 6/2010 | Gharib et al. |
| 2011/0036212 | A1* | 2/2011 | Santamarina ......... B25B 15/001 81/436 |
| 2012/0053597 | A1 | 3/2012 | Anvari et al. |
| 2012/0116265 | A1 | 5/2012 | Houser et al. |
| 2014/0148808 | A1 | 5/2014 | Inkpen et al. |
| 2015/0066030 | A1 | 3/2015 | McGinley et al. |
| 2015/0088183 | A1 | 3/2015 | Vipperman et al. |
| 2015/0216541 | A1 | 8/2015 | Schmieding et al. |
| 2016/0361070 | A1 | 12/2016 | Ardel et al. |

FOREIGN PATENT DOCUMENTS

| | | | |
|---|---|---|---|
| WO | WO 2015006296 | * 1/2015 | ............. A61B 17/16 |
| WO | WO 2015/014771 | 2/2015 | |
| WO | WO 2016/199152 | 12/2016 | |
| WO | WO 2016/199153 | 12/2016 | |

OTHER PUBLICATIONS

International Search Report and the Written Opinion dated Sep. 28, 2016 From the International Searching Authority Re. Application No. PCT/IL2016/050612.
Restriction Official Action dated Sep. 2, 2016 From the US Patent and Trademark Office Re. U.S. Appl. No. 15/177,692.
Aston University "Bone Drill", Aston University, Birmingham, UK, Business Partnership Unit, Commercial Opportunity, 2 P., 2007.
McGinley "IntelliSense™ Drill", McGinley Orthopaedic Innovations, Engineering Medical Progress, 69th ASSH Annual Meeting, New Product Showcase, Boston, ML, Sep. 18-20, 2014, p. 1-3, Sep. 2014.
Official Action dated Nov. 22, 2016 From the US Patent and Trademark Office Re. U.S. Appl. No. 15/177,692. (15 pages).
Official Action dated Mar. 29, 2017 From the US Patent and Trademark Office Re. U.S. Appl. No. 15/177,692. (30 pages).
Applicant-Initiated Interview Summary dated May 23, 2017 From the US Patent and Trademark Office Re. U.S. Appl. No. 15/177,692. (3 pages).

* cited by examiner

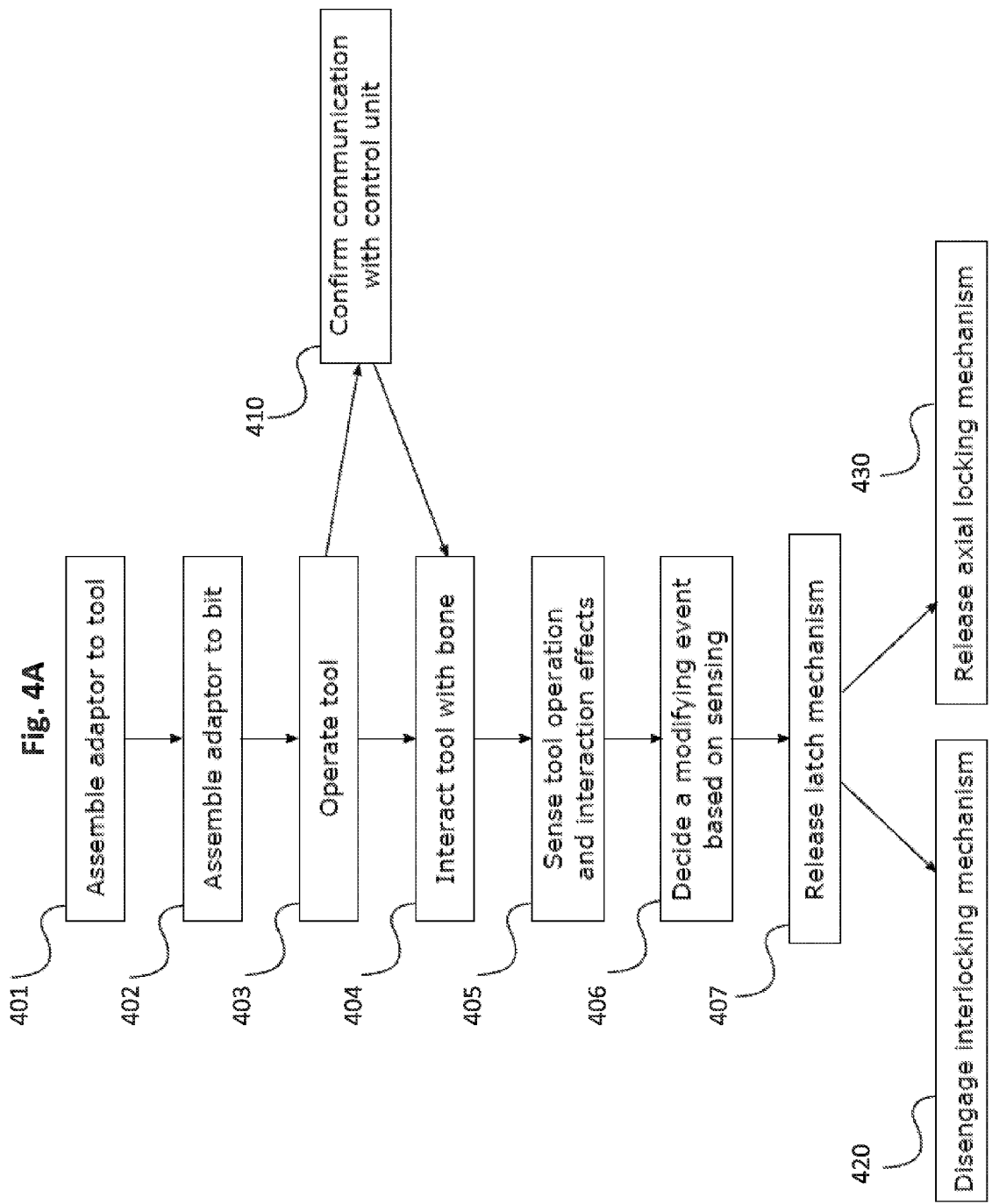

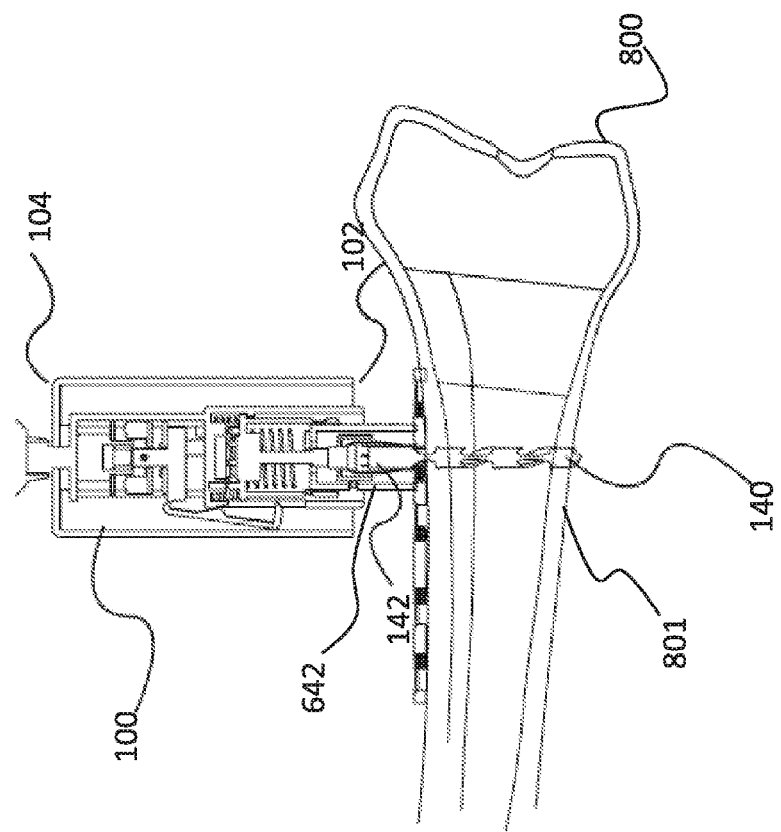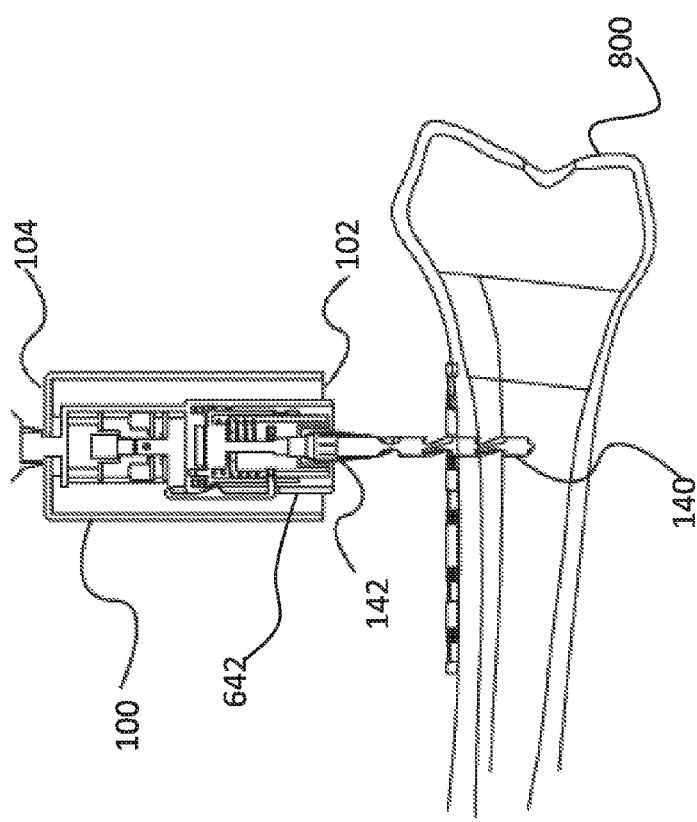
Fig. 8A
Fig. 8B

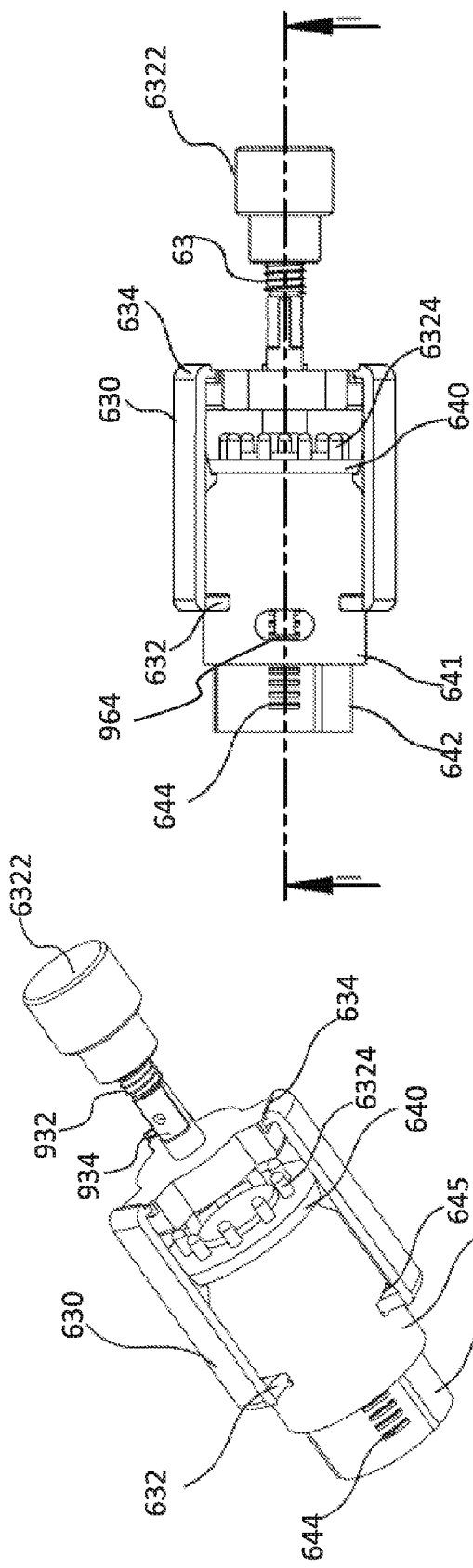
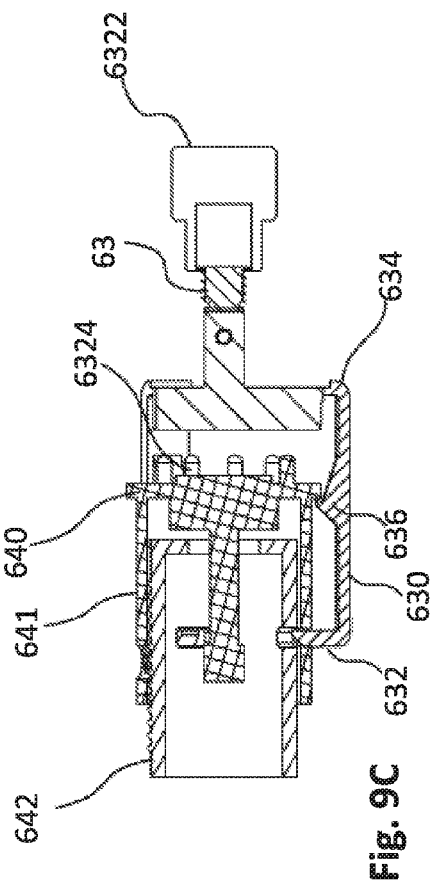
Fig. 9A
Fig. 9B
Fig. 9C

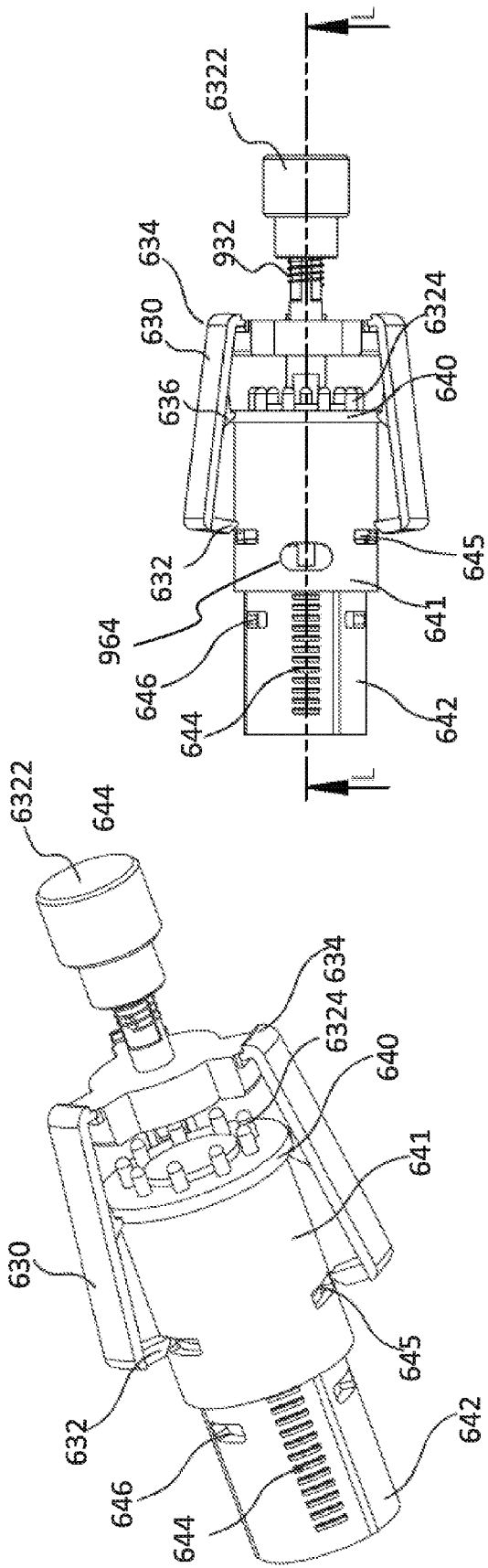
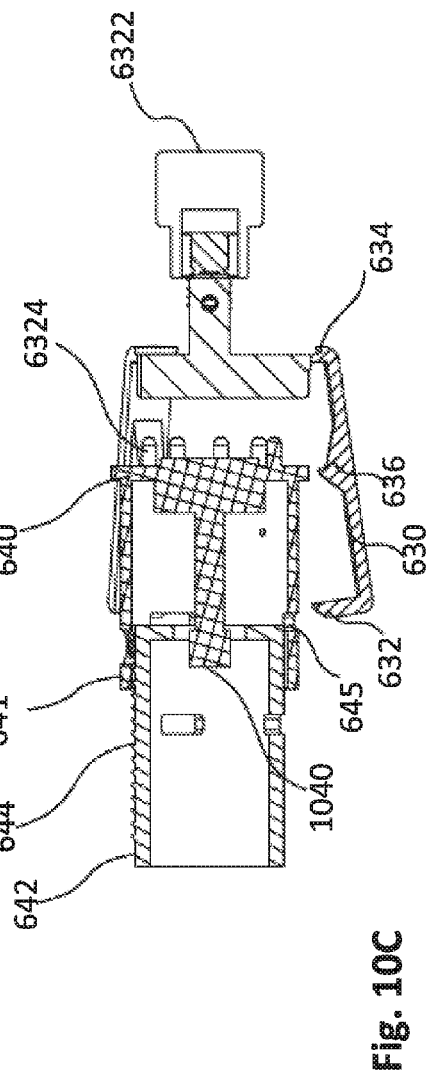
Fig. 10A
Fig. 10B
Fig. 10C

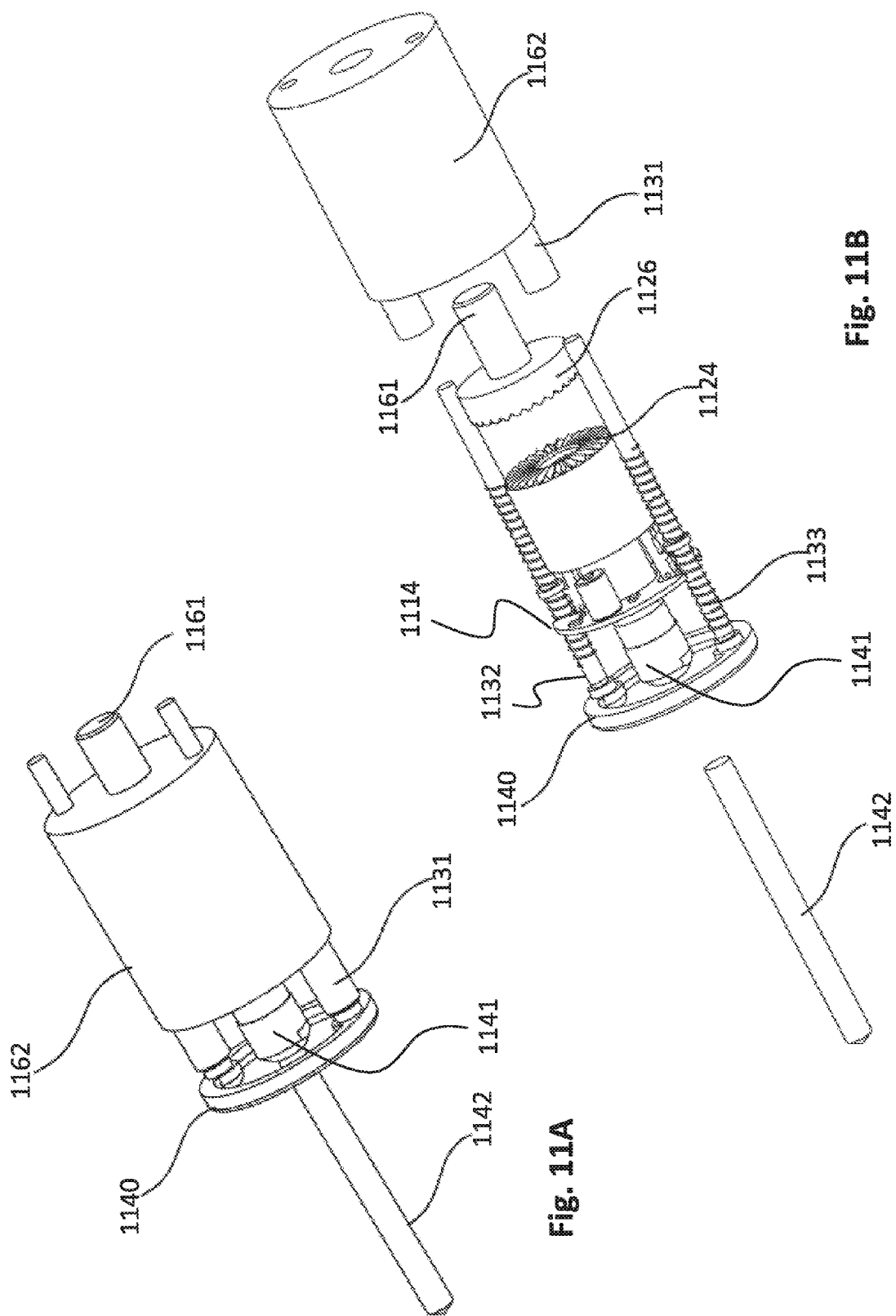

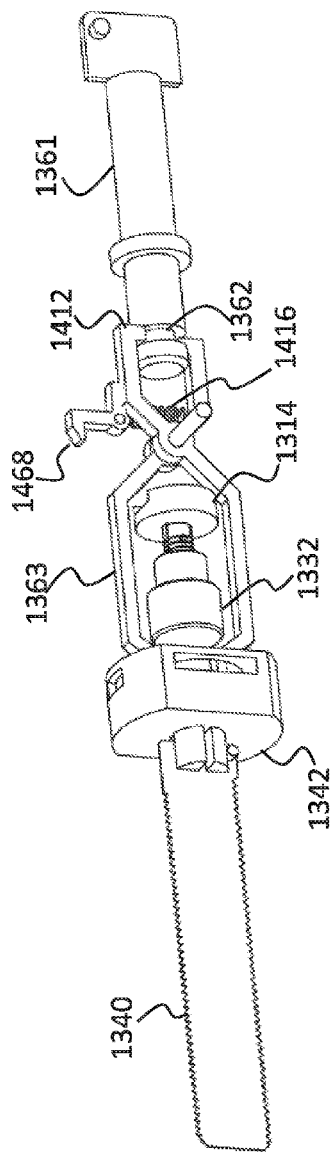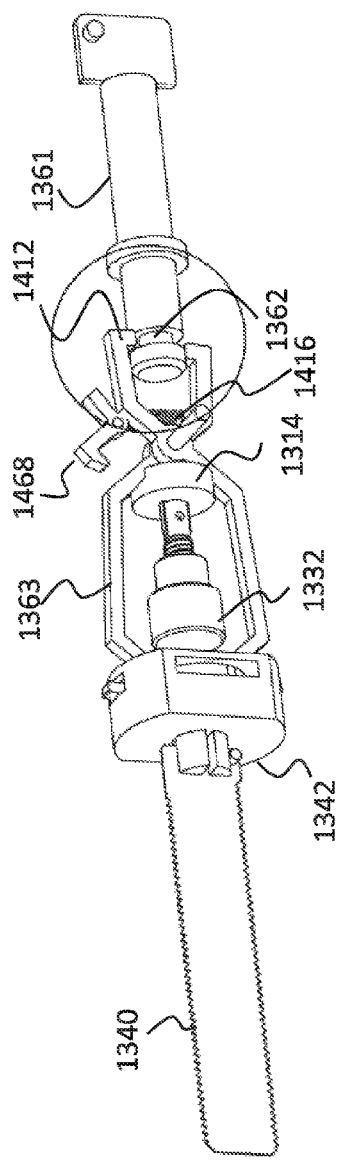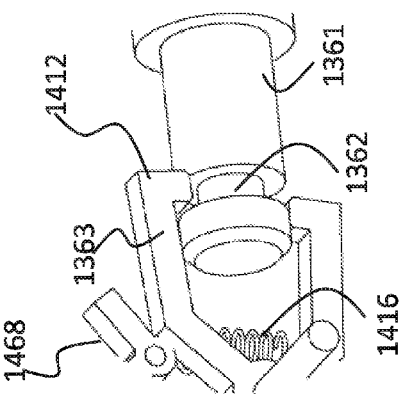
Fig. 14C
Fig. 14D
Fig. 14E

DEVICE FOR MODIFYING THE OPERATION OF SURGICAL BONE TOOLS AND/OR METHODS THEREOF

RELATED APPLICATIONS

This application claims the benefit of priority under 35 USC 119(e) of U.S. Provisional Patent Application No. 62/173,365 filed on Jun. 10, 2015.

This application is also related to co-filed, co-pending and co-assigned PCT Patent Application entitled "DEVICE FOR MODIFYING THE OPERATION OF SURGICAL BONE TOOLS AND/OR METHODS THEREOF" (Attorney Docket No. 65467) by Ehud ARDEL and Shlomo DAVID, claiming priority of U.S. Provisional Patent Application No. 62/173,365 filed on Jun. 10, 2015, the contents of which are incorporated herein by reference in their entirety.

FIELD AND BACKGROUND OF THE INVENTION

The present invention, in some embodiments thereof, relates to an apparatus for use with a surgical bone tool and, more particularly, but not exclusively, to a system, a device and methods thereof, for modifying the operation of surgical bone tools.

Scuola Superiore Di Studi University disclosed in U.S. Pat. No. 6,033,409 "a surgical drill comprising a rotating head having a drill bit suitable to bore a body and support means to which the head is pivotally connected. An actuating unit of the movement of the drill bit with respect to the body to bore is provided for, comprising a first support comprising the head and a second support, suitable for resting directly upon the body and translating with respect to the first support parallel to the drill bit. The movement between drill bit and body is caused by the relative movement between drill bit and second support. Means for the detection of the force acting on the drill bit and means for the control of the drill bit displacement in function of the drilling force are provided for. The drill, manually holdable, presents both a reference with respect to the patient body and allows a precise control of the drill bit displacement".

Hsu et al., disclosed in U.S. Pat. No. 6,336,931 "an automatic bone drilling apparatus for surgery operation using a computer to control a hand tool drilling device to drill opening in skeleton. The computer has a fuzzy logic software to control the hand tool operation through a control box and a manual-automatic mode switch box. The hand tool drilling device may be securely mounted on the patient. Drilling location and size and depth may be precisely controlled to enhance surgical operation safety".

U.S. Pat. No. 8,463,421 discloses a method of "drilling a hole in a workpiece in order to control breakthrough of the workpiece comprising the steps of: a) initiating contact between a drill bit of a drill unit and the workpiece; b) operating the drill unit to rotate the drill bit to drill the workpiece; c) during drilling of the workpiece measuring the force, F and torque, T, experienced by the drill bit; d) calculating a variable F', based on the measured force, F, representing the rate of change of F; e) calculating a variable, T' based on the measured torque, T, representing the rate of change of T; f) calculating a variable F" representing the rate of change of F'; g) calculating a variable T" representing the rate of change of T"; h) detecting the onset of breakout of the workpiece by use of the variables F', F", T' and T"; i) thereby controlling the speed of rotation of the drill bit during breakthrough of the workpiece to control the degree of breakout of the drill bit from the workpiece".

Additional background art includes U.S. Patent Application Publication No. US2014148808, International Patent Application No. WO2015014771, U.S. Pat. No. 8,926,614, CN Patent No. CN101530341, U.S. Patent Application Publication No. US2015066030, U.S. Patent Application Publication No. US2015088183, U.S. Patent Application Publication No. US2005131415, U.S. Patent Application Publication No. US20050116673 and U.S. Pat. No. 8,821,493.

SUMMARY OF THE INVENTION

Following are some examples of some embodiments of the invention:

Example 1

An adaptor for modifying the operation of a surgical bone-tool, comprising:

a housing having a distal end and a proximal end coupled between a chuck and an operating bit of the tool, such that force generated by a motor of the tool is delivered to the operating bit through the adaptor;

a clutch, contained in the housing, having an engaged and a disengaged configurations, respectively interconnecting and disconnecting the chuck to the operating bit; the clutch automatically disengages in response to an electric current, causing a cutoff of the force delivery;

wherein the housing comprises a proximal fastener, sized and shaped to connect with the operating bit and a distal fastener, sized and shaped to connect with the chuck.

Example 2

The adaptor according to example 1, wherein the housing is connected to the tool and the bit, only by the fasteners and it freely rotates in conjunction with a rotating motion generated by the motor.

Example 3

The adaptor according to example 1, wherein the housing is stationary, while the fasteners and chuck rotate in conjunction with a rotating motion generated by the motor.

Example 4

The adaptor according to example 1, wherein the force delivery is provided without modifying the force.

Example 5

The adaptor according any of examples 1-4, further comprising a latch mechanism having two activation states, and wherein a transition in the activation state results in the engagement or disengagement of the mechanical interlocking mechanism.

Example 5

The adaptor according to example 4, wherein the latch mechanism is a magnetic solenoid latch.

Example 6

The adaptor according to example 5, wherein the clutch comprises at least two members having interlocking interfaces.

Example 7

The adaptor according to example 6, wherein the interfaces comprises complementary geometries.

Example 8

The adaptor according to example 7, wherein the interfaces comprises a plurality of complementary pins and cavities.

Example 9

The adaptor according to example 6, wherein at least one of the interfaces comprises a magnetic material.

Example 10

The adaptor according to example 6, wherein in the engaged configuration the at least two interfaces are compressed together against a resistance.

Example 11

The adaptor according to example 10, wherein the resistance is a spring or compressed air, or both.

Example 12

The adaptor according to example 11, further comprising a stopping spacer providing a cutoff of the axial forces delivered to the bit.

Example 13

The adaptor according to example 12, wherein the stopping spacer comprises at least two members, at least partially overlapping along the proximal-distal axis of the adaptor.

Example 14

The adaptor according to example 13, wherein at least one of the members comprises a locking member to mechanically fix the members together against a resistance.

Example 15

The adaptor according to example 12, comprising at least one fastener coupling the clutch and the stopping spacer against a resistance.

Example 16

The adaptor according to example 15, wherein the fastener comprises a hinge, enabling tilting of the fastener away from the coupling.

Example 17

The adaptor according to example 16, wherein the transition of the latch mechanism translates the fastener in the proximal-distal axis of the adaptor, resulting in the tilting of the fastener and its release from the coupling.

Example 18

The adaptor according to example 10, further comprising a manually operated locking mechanism preventing the release of the resistance.

Example 19

The adaptor according to example 1, further comprising a battery source selected from a group consisting of lithium battery, metal-air battery, polymer gel, aluminum based and any combination thereof.

Example 20

The adaptor according to example 1, further comprising a chargeable battery source comprising a supercapacitor charging when operating the tool.

Example 21

The adaptor according to example 1, wherein the adaptor is suitable for disposable use.

Example 22

A system for monitoring and modifying a surgical bone tool operation, comprising:
  an adaptor according to example 1;
  at least one sensor; and
  at least one control circuit.

Example 23

The system according to example 22, wherein the sensor is comprised in the adaptor.

Example 24

The system according to example 23, wherein the sensor is selected from the group consisting of Torque sensor, Pushing/pulling force sensor, Radial velocity sensor, Three dimensional Accelerometer sensor, Three dimensional Tilt sensor and any combination thereof.

Example 25

The system according to example 22, wherein the sensor comprises a distance sensor located at the proximal end of the tool bit.

Example 26

The system according to example 25, wherein the distance sensor is an ultrasound transducer and ultrasound waves are transmitted through the bit.

Example 27

The system according to any of example 22-26, wherein the sensor comprises one or more non-contact temperature sensors.

Example 28

The system according to example 27, wherein at least one the one or more non-contact temperature sensors is located externally to the adaptor.

Example 29

The system according to example 28, wherein at least one the one or more non-contact temperature sensors is located embedded within the adaptor.

Example 30

The system according to example 22, wherein the control circuit is comprised in the adaptor.

Example 31

The system according to example 30, wherein the control circuit comprises instructions for executing a stopping event.

Example 32

The system according to example 31, wherein the executing a stopping event comprises instructions for transitioning between the states of the latch mechanism.

Example 33

The system according to any of examples 31-32, wherein the executing a stopping event comprises instructions for activating an alert.

Example 34

The system according to example 33, wherein the alert is in a form selected from a group consisting of a visual notification, an audio notification and a vibratory notification.

Example 35

The system according to example 31, wherein the control circuit further comprises at least one of a wireless receiver, a wireless transmitter and a wireless transceiver.

Example 36

The system according to example 31, wherein the control circuit comprises a processor having instructions to analyze sensory data transmitted from the at least one sensor.

Example 37

The system according to example 36, wherein the control circuit executes a stopping event when the analyzed sensory data indicates at least one of:
 a. identification of cortical bone breakthrough;
 b. identification of cortical bone penetration;
 c. identification of trabecular bone penetration; and
 d. identification of a predetermined depth range.

Example 38

The system according to example 36, wherein the control circuit executes a stopping event when the analyzed sensory data indicates temperature of the bit above a predetermined threshold.

Example 39

The system according to example 36, wherein the control circuit executes a stopping event when the analyzed sensory data indicates temperature of the bone above a predetermined threshold.

Example 40

The system according to example 22, wherein the operating tip further comprises illumination means transmitting light through a path of the bone penetration.

Example 41

The system according to example 22, comprising a control circuit located externally to the adaptor.

Example 42

The system according to example 22, comprising a sensor unit located externally to the adaptor.

Example 43

The system according to example 36, wherein the processor analyzes sensory data in view of a database containing data selected from the group consisting of general bone characteristics, patient personal information, patient body part dimensions and any combination thereof.

Example 44

The system according to example 22, further comprising at least one display mounted on the adaptor.

Example 45

The system according to example 22, further comprising at least one display mounted on the adaptor.

Example 46

The system according to example 22, further comprising at least one display for presenting the sensory data analysis.

Example 47

The system according to example 22, wherein the tool is a drill or a saw.

Example 48

The system according to example 22, wherein the tool robotic ally operated.

Example 49

A method for modifying the operation of a surgical bone-tool, comprising:
 coupling a clutch between a chuck and an operating bit of the tool;

interacting a bone region with the operating bit by delivering forces generated by a motor of the tool to the operating bit through the adaptor; and transmitting an electrical current causing disengagement of the clutch;

wherein the coupling comprises connecting a proximal portion of the clutch to the operating bit and connecting a distal portion of the clutch to the tool chuck.

Example 50

The method according to example 49, comprising sizing and shaping the proximal portion to accommodate an operating bit.

Example 51

The method according to any of examples 49-50, comprising sizing and shaping the distal portion to fit into a tool chuck.

Example 52

The method according to example 49, further comprising stopping a radial motion of the operating tip.

Example 53

The method according to example 49, further comprising stopping an axial motion of the operating tip.

Example 54

The method according to example 49, further comprising stopping a vibrational motion of the operating tip.

Example 55

The method according to example 49, further comprising reloading by re-engaging the clutch module with the main shaft.

Example 56

The method according to example 49, further comprising transmitting the electrical current when detecting breakthrough of the bit through the bone.

Example 57

The method according to example 49, further comprising transmitting the electrical current when detecting a bone penetration having a predetermined depth.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as determining the contact force between a wheel and a surface, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-B are flow charts of two exemplary processes of determining interaction cessation, according to some embodiments of the invention, in which FIG. 4A represents an exemplary process of an algorithm for determining a stopping event, and FIG. 4B represents an exemplary method of using the system provided herein;

FIGS. 6A-B are schematic views of an exemplary adaptor configuration, according to some embodiments of the invention, wherein FIG. 6A illustrates a schematic side view of the exemplary adaptor and FIG. 6B illustrates a schematic explosive view of the exemplary adaptor;

FIGS. 7A-B are schematic cross-sectional side views of an exemplary mechanical interface of an adaptor configured for a drill, according to some embodiments of the invention, wherein FIG. 7A illustrates an engaged configuration and FIG. 7B illustrates a disengaged configuration;

FIGS. 8A-B are schematic cross-sectional side views of an exemplary use of an adaptor with a drill, according to some embodiments of the invention, wherein FIG. 8A illustrates an engaged configuration and FIG. 8B illustrates a disengaged configuration;

FIGS. 9A-C are schematic views of an exemplary mechanical interlocking interface having an engaged configuration, according to some embodiments of the invention, wherein FIG. 9A illustrates a perspective view, FIG. 9B illustrates a side view and FIG. 9C illustrates a cross-sectional side view, according to line 1 in FIG. 9B;

FIGS. 10A-C are schematic views of an exemplary mechanical interlocking interface having a disengaged configuration, according to some embodiments of the invention, wherein FIG. 10A illustrates a perspective view, FIG. 10B illustrates a side view and FIG. 10C illustrates a cross-sectional side view, according to line L in FIG. 10B;

FIGS. 11A-B are schematic views of another exemplary mechanical interlocking interface, according to some embodiments of the invention, wherein FIG. 11A illustrates a perspective view and FIG. 11B illustrates an explosive view;

FIGS. 12A-B are schematic cross-sectional side views of the exemplary mechanical interlocking interface illustrated in FIGS. 11A-B, according to some embodiments of the invention, wherein FIG. 12A illustrates an engaged configuration and FIG. 12B illustrates a disengaged configuration;

FIGS. 14A-E are schematic cross-sectional side views and perspective views of an exemplary mechanical interlocking interface of the adaptor as illustrated in FIG. 13, according to some embodiments of the invention, wherein FIG. 14A illustrates a cross-sectional side view of an engaged configuration, FIG. 14B illustrates a cross-sectional side view of a disengaged configuration, FIG. 14C illustrates a perspective view of an engaged configuration, FIG. 14D illustrates a perspective view of a disengaged configuration and FIG. 14E illustrates an enlargement of the circular inset shown in FIG. 14D.

DESCRIPTION OF SPECIFIC EMBODIMENTS OF THE INVENTION

Figure 1:
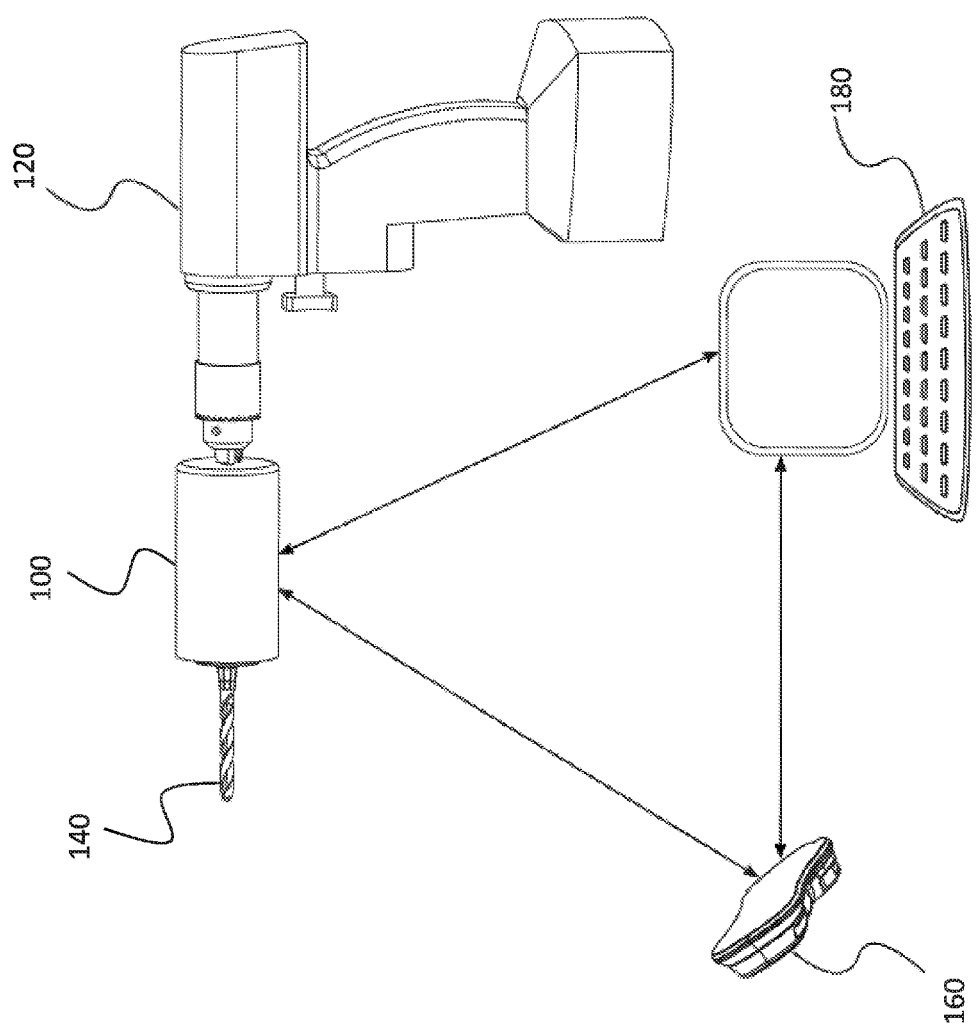
FIG. 1 is an exemplary high level overview of a system comprising an adaptor for use with a surgical tool, a sensor unit and a control circuit, according to some embodiments of the invention.

The present invention, in some embodiments thereof, relates to an apparatus for use with a surgical bone tool and, more particularly, but not exclusively, to a system, a device and methods thereof, for modifying the operation of surgical bone tools. As used herein, bone refers to any rigid organ, including, but not limited to, skull, spine, skeleton, teeth and cartilage.

Overview

An aspect of some embodiments of the invention relates to an adaptor for coupling to a surgical bone tool and for mechanically intermediating the surgical tool motor and the surgical tool bit.

In some embodiments, the adaptor is coupled to the surgical tool by fasteners and/or clamps which are sized and shaped to connect to an existing member and/or plug of the surgical tool. Optionally, the existing member and/or plug is a standard fastener for use with surgical tools. In some embodiments, the adaptor is coupled to the surgical tool using only the tool's existing plugs, and without the use of additional support. Alternatively or additionally, the adaptor is connected in its distal side to a distinct position in the tool, such as for example the top surface of the tool.

In some embodiments, by mechanically intermediating, the adaptor allows forces generated by the motor to be transmitted to the tool bit. In some embodiments, the adaptor comprises a mechanical cutoff mechanism to terminate force transmission to the tool bit. In some embodiments, the mechanical cutoff is provided automatically upon receiving a signal.

An aspect of some embodiments of the invention relates to a surgical tool adaptor having proximal and distal portions, at least one of which comprising at least one fastener sized and shaped to be connected with a surgical tool. In some embodiments, a bit fastener is provided to couple the adaptor to the surgical tool operating bit. Alternatively or additionally, a chuck fastener is provided to couple the adaptor to the surgical tool chuck. Alternatively or additionally, a shaft fastener is provided for directly coupling the adaptor to a motor shaft of the tool.

In some embodiments, the bit fastener is shaped and sized to mimic the existing surgical tool chuck. In some embodiments the chuck fastener is shaped and sized to mimic the surgical tool bit. It is a potential advantage to provide fasteners which simulate fasteners and clamps already provided with the surgical tool, likely enabling to couple the adaptor in a modular fashion to any commercially available surgical tool, without having first to modify the tool or provide additional adaptors. It is another potential advantage to have an adaptor connecting to the tool at a single location, without having to further secure it with a second connection.

In some embodiments, only the proximal portion of the adaptor is provided with a fastener, while the distal portion of the adaptor is premanufactured to comprise a surgical tool bit. Alternatively, only the distal portion of the adaptor is provided with a fastener, while the proximal portion of the adaptor is premanufactured interconnected with the surgical tool's body.

In some embodiments, a variety of adaptors having a common proximal fastener, for coupling to a surgical tool body, are each provided with a different tool bit preassembled at the distal portion. Optionally, the proximal fastener is shaped and sized to mimic the tool bit portion preassembled at the distal portion, such that the adaptor may be connected to the surgical tool as if it were the bit itself. It is a potential advantage to provide the adaptor having the surgical tool bits preassembled, enabling a familiar setup configuration for the surgeon with minimal modifications for the surgical routine.

In some embodiments, the adaptor is assembled such that rotational forces generated by the motor cause the adaptor, and its components, to rotate together with the bit. In some embodiments, the adaptor is provided with a housing, and only some of its components are rotated by the motor.

In an exemplary embodiment, the tool is a surgical bone drill, and the adaptor is connectable to the drill chuck in its distal end and to the drill bit in its proximal end, such that forces from the drill motor are delivered to the drill bit, optionally without force modification. Alternatively, the tool is a surgical bone saw or cutting device, and the adaptor is connectable to the saw chuck in its distal end, and to the saw bit in its proximal end.

An aspect of some embodiments of the invention relates to a surgical bone tool adaptor having a mechanical cutoff mechanism. In some embodiments, the cutoff mechanism prevents rotational forces generated by the tool motor to transmit to the tool bit, i.e. a clutch. Alternatively or additionally, the cutoff mechanism prevents axial forces originating in the tool's body from reaching to the tool bit, i.e. a spacer to mechanically obstruct the patient's body from the tool, preventing further advancement of the tool with the bit into the bone.

In some embodiments, rotational forces are transmitted by the adaptor through a mechanical interlocking mechanism, mechanically intermediating the surgical tool's motor shaft and the tool's bit. In some embodiments, the interlocking mechanism comprises at least two members, each having an interface configured to geometrically fit with one another. In some embodiments, disengagement of the interlocked interfaces causes a cutoff of the rotational force transmission to the tool bit.

In some embodiments, the interlocking interfaces are compressed towards one another, optionally being held together by magnetic forces. In some embodiments, a magnetic pole piece is coupled to at least one of the interlocking members. Alternatively or additionally, a magnetic pole is embedded in at least one of the interlocking members. Alternatively or additionally, at least one of the interlocking interfaces is provided having magnetic properties.

In some embodiments, the magnetic components are holding the interlocking members compressed towards each against a spring. Alternatively or additionally, compression is provided against air pressure.

In some embodiments, release of the compressed state of the interlocking members is provided by masking the magnetic forces. Optionally, masking is provided by a magnetic solenoid latch, which upon electrical stimulation provides a magnetic induction which negates the magnetic field provided by the above mentioned magnetic forces. Optionally, release of the interlocked members is provided by a centrifugal force.

In some embodiments, the adaptor is provided having an axial force cutoff mechanism. Preventing axial force transmission potentially assists in limiting the surgeon's applied force. In some embodiments, at least two axial members are provided, extending along the proximal-distal axis of the adaptor, optionally telescopically aligned. In some embodiments, the members are shaped as canisters at least partially fitted to overlap, optionally telescopically wise. In some embodiments, the axial members couple the proximal portion of the adaptor and its distal portion.

In some embodiments, the members are compressed towards each other against a compression means, such as at least one spring. In some embodiments, the two members are held compressed by magnetic forces, optionally the same magnetic forces which hold together the abovementioned interlocking members. Alternatively or additionally, the members are held together with a locking clasp. Alternatively or additionally, the members are held together with a ratchet mechanism, optionally wherein one member, or both, is unidirectional and one member, or both, is elastic.

In some embodiments, the device uses electrical power to perform the disengagement of the clutch. Optionally, electrical power is provided by a battery.

Optionally, the battery is configured to operate for a relatively short period of time, optionally for at least a typical duration of a bone surgery, causing the device to be a disposable device, optionally for a single use only. Alternatively, the device is configured to be sterilized for multiple uses. In some embodiments, electrical power is provided to the device through the operation of the surgical tool motor, by using, as a non-limiting example, a super capacitor.

In some embodiments, the mechanical interlocking mechanism may be reset to its initial configuration, optionally by reverse operating the tool's motor. For example, if the surgeon would like to continue the tool's operation even after the automatic cutoff has been activated. Alternatively or additionally, the mechanical interlocking mechanism needs to be manually compressed back to its original state. Alternatively or additionally, the mechanical interface, for example the axial members, cannot be compressed back to the initial configuration, rendering the adaptor as disposable, for a one-time use only.

An aspect of some embodiments of the invention relates to modifying a surgical tool's operation by the above mentioned adaptor upon receiving a signal. In some embodiments, operation modification is provided by a control circuitry. In some embodiments, the control circuitry comprises instructions for releasing the compressed configuration of the rotational force transmission interface, or the axial force transmission interface, or both. Alternatively or additionally, the control circuit provides an alert, which could be in some embodiments visual, and/or auditory, and/or vibrational.

In some embodiments, the control circuitry sends instructions when detecting a modifying event. In some embodiments, modifying is done by cutting off the power transmission to the tool bit. Alternatively, modifying is done by attenuating the power transmission to the tool bit. Alternatively or additionally, modifying results in setting off an alarm.

In some embodiments, a modifying event is when the tool bit breaks through the cortical bone, optionally at the distal portion of the bone i.e. the portion furthest from the tool interaction location. Alternatively or additionally, a modifying event is when the tool bit transfers from one tissue to another, such as for a non-limiting example, when transferring from the trabecular bone tissue to the cortical bone tissue. Alternatively or additionally, a modifying event is detecting that tissue breakthrough is going to occur within T seconds or X mm. Optionally T is between 1-5 seconds, 2-4 seconds, 3 seconds, or any range larger, smaller or intermediate to these ranges. Optionally X is between 1-5 mm, 2-4 mm, 2-3 mm, or any range larger, smaller or intermediate to these ranges. Alternatively or additionally, a modifying event is upon detecting a mechanical problem with the tool.

In some embodiments, the control circuitry is embedded within the adaptor, optionally in proximity to the mechanical interlocking mechanism. Alternatively or additionally, the control circuitry is externally from the tool. In some embodiments, the control circuitry comprises communication means, a transmitter and/or a receiver.

Optionally, the communication means operate wirelessly. In some embodiments, the communication means is based on a hand shake protocol.

In some embodiments, proper communication is verified by operating the tool prior to its interaction with the bone, and testing the mechanical cutoff take place, assuring that instructions are properly communicated to and/or properly transmitted from the control circuitry.

In some embodiments, the automatic cutoff provided by the control circuit is manually turned off. Alternatively or additionally, the automatic cutoff is automatically turned off, such as when the surgeon continues operating even after the cutoff has been activated, such as when reversely initiating the mechanical configuration of the adaptor.

In some embodiments, the control circuit is provided with a user interface. In some embodiments, the user interface is in the form of a display, optionally embedded onto the adaptor's external covering. Alternatively or additionally, the display is provided in an external computer, such as a personal computer, tablet, smartphone, server and the like. In some embodiments, the user interface allows the surgeon to input operation parameters prior to the surgery. Alternatively or additionally, the user interface is used for displaying to the surgeon the interaction progress of the tool with the bone, such as depth measurements. Alternatively or additionally, the display graphically presents both the tool and the bone, optionally in real time.

In some embodiments, the control circuit comprises a memory component, optionally to store monitored operations. In some embodiments, data from previously stored operations is used for detecting a modification event of the tool.

An aspect of some embodiments of the invention relates to overriding the operation instructions provided to a surgical tool, by using the abovementioned adaptor having the control circuitry. In some embodiments, the instructions provided by the control circuitry influence the mechanical configuration of the adaptor regardless of the power transmitted by the tool.

In some embodiments the power transmitted by the tool is provided by manually operating the operation switch of the tool by a user. Alternatively the power transmitted by the tool is provided in an automatic manner by a robotic algorithm.

In some embodiments, instructions for cutting the power supplied by the tool are based on a predetermined protocol.

Optionally, the predetermined protocol is based on a database having a plurality of hard tissue interaction profiles.

An aspect of some embodiments of the invention relates to a modifying a surgical tool's operation by the above mentioned adaptor upon receiving a signal based on sensory input. In some embodiments, the abovementioned control circuitry detects a tool operation modifying event based on input from a sensor unit, having at least one sensor.

In some embodiments, a sensor unit is embedded within the adaptor. Alternatively or additionally, a sensor unit is located externally to the adaptor and within the surgical tool. Alternatively or additionally, a sensor unit is located externally to the adaptor and externally to the surgical tool. In some embodiments, the sensor unit is mounted on the patient, optionally in proximity to the surgery region, optionally in a substantially opposite position to the tool's interaction site.

Alternatively or additionally, a sensor unit is positioned on the surgeon's operating hand. Alternatively or additionally, a sensor unit is located in a remote location in the room where the surgery takes place, optionally, as an example, on the patient's bed.

In some embodiments, the sensor unit detects tool related mechanical parameters. For example, in some embodiments the sensor unit includes a torque sensor to measure the torque produced by the tool's motor, optionally between the tool's chuck and its operating tip. Alternatively or additionally, the sensor unit includes an axial force sensor to detect pushing and/or pulling forces, i.e. measure positive or negative axis force, optionally produced at the tool bit. Alternatively or additionally, the sensor unit includes a radial velocity sensor for measuring the motor and/or the bit's rotating speed.

In some embodiments, a battery power consumed sensor is provided to detect the power used by the tool. Optionally, detecting the power consumed by the tool indicates the force applied by the tool, potentially suggesting the tool's interaction extent with the bone.

In some embodiments, the sensor unit comprises a three-dimensional accelerometer sensor, potentially for detecting body vibrations when mounted on the patient's body, optionally, configured to detect frequencies of less than 20 Hz. In some embodiments, a three-dimensional accelerometer is provided in a sensor unit when embedded in the surgical tool. Optionally, radial force measured in three dimensions by the accelerometer is used to detect trembling of the adaptor and/or the tool.

In some embodiments, the sensor unit comprises a range finder, optionally when the apparatus is housed within the tool, potentially used to determine the distance of the tool, optionally the tool's tip, from the patient's bone. In some embodiments, the range finder is based on infrared technology. Alternatively or additionally, it is based on ultrasound. In some embodiments, ultrasound transmission is provided through the tool bit.

In some embodiments, the sensor unit comprises a magnetometer, optionally when the apparatus is mounted on the patient's body, and potentially used for detecting the presence of the tool's tip, such that, for example, as the tool progresses along the bone, the tool's tip detection in the magnetometer increases.

In some embodiments, the sensor unit comprises a non-contact temperature sensor, optionally for detecting the interaction site of the tool with the bone. Interacting the tool bit with the bone potentially leads to overheating of the surgery region. In some embodiments, detection of a temperature higher than a predetermined threshold leads to the initiation of the mechanical cutoff mechanism, either radial, axial or both.

In some embodiments, sensors in the sensor unit are based on Piezo-Electric technology, having the potential advantage of measuring sensory data in small factors and light weight elements, enabling a design of the adaptor to be relatively light and small sized, potentially causing as little interference to the surgeon.

An aspect of some embodiments relates to a system for controlling the operation of a surgical bone tool, and configured to automatically cutoff the action of an operating tip of the tool upon receiving a signal. The system comprises the abovementioned adaptor, the control circuitry and the sensor unit. In some embodiments, the control circuitry comprises a computer. Optionally, the computer communicates with the mechanical interface in the adaptor, optionally in addition to communicating with the sensor unit. In some embodiments, the computer analyzes sensory data transmitted by the sensor unit and decides based on the analysis what instructions to transmit to the adaptor.

An aspect of some embodiments relates to a method for measuring a bone penetration depth. In some embodiments the measurement is performed in conjunction with the operation of the surgical tool. In some embodiments, measurement is provided by monitoring the forces exerted by the surgical tool. In some embodiments, the measurement data is used for correlating with an appropriate screw size. In some embodiments, the screw size and/or penetration depth is graphically presented on a display, optionally comprised within the abovementioned adaptor.

An aspect of some embodiments relates to a method to selectively process a hard tissue.

In some embodiments, the bone drilling system is composed of a driller with drilling bit, optionally fitted over an add-on adaptor in between and/or embedded within the driller itself. In some embodiments, is provided a sensor unit, i.e. a Bio-Medical patch, and/or at least one designated sensor, optionally mounted upon the organ and/or in any other location that enables it to sense and/or get the needed related information. In some embodiments, the adaptor and/or the sensor is connected to a controller computer in various configurations.

In some embodiments, within the add-on adaptor there is a set of sensors, optionally, for example, composed of any combination of the following:

a. Torque sensor optionally to measure the torque produce by the driller engine between driller original chuck and the tip of the driller bit b. Pushing/pulling force sensor optionally to measure the axis force (positive or negative) that is produced at the drill bit tip c. Radial velocity sensor (RPM) optionally to measure the drilling bit rotating speed d. Driller battery power consumed sensor optionally connected in line to the drilled battery and optionally measures and power (W) that is consumed by the driller engine. Optionally measuring current (Ampere) and voltage (Volt) will yield the power (Watts) supplied e. 3 Dimensions accelerometer sensor that is optionally used to measure radial force measured in the add-on adaptor in all 3 dimensions (X, Y, Z). Optionally this is used to track trembling of the adaptor f. 3 Dimensions tilt sensor that is optionally used to measure the adaptor tilt comparing to the horizon g. Microphone (magnetic or piezoelectric) optionally to pick up audio waves of frequencies from 100 Hz to 5 KHz h. Electro mechanical axial clutch, that is optionally used to cut the drilling power to the drilling tip In some embodiments, at least one of the add-on adaptor sensors is based on Piezo-Electric devices and/or any other sensing technology that measures the information in small factor and/or light weight elements optionally allowing designing of the adaptor add-on in a light, small size and/or short manner that will cause as little interferences to the surgeon working and driller handing comparing to his current way of work. In some embodiments, the connection to the driller battery is also used to run the internal add-on adaptor electronics.

In some embodiments, all of the above is part of a semi-automated/fully automated drilling/cutting device (optionally embedded within the system and/or part of it).

In some embodiments, add-on adaptor rotational sensors deliver their data to the Add-on adaptor controller board (optionally a non-moving part at the fixed side of the Add-on Adaptor), optionally by the use of conductive slippery rings and/or by the use of laser signal transferring between moving and non-moving parts of the add-on Adaptor.

In some embodiments, the add-on adaptor measures all signals from the sensors and/or checks the changes over time (derivatives of the signals). In some embodiments, using this information the controller computer can recognize specific signals pattern that are potentially unique to bone cortical penetration. In some embodiments, the controller computer is preconfigured with all types of bones information and/or human bones attributes. In some embodiments, the surgeon configures the controller prior to the surgery start, optionally with the specific information of the patient information and/or surgery type, such that the controller will know what pattern to track.

In some embodiments, upon pattern positive identification, the controller sends a signal to the add-on adaptor to initiate an LED light and/or Buzzer and/or any other notification and/or automatic drilling rotating stop, optionally by using the add-on adaptor internal clutch.

In some embodiments, the signals of the add-on adaptor sensors are being sampled, and/or filtered, and optionally sent to the controller computer. Optionally the information will be transferred to the controller computer by the use of wired or wireless communications path, such as Wi-Fi, Bluetooth, ZigBee or similar.

In some embodiments, an external sensor unit is used such as provided in PCT Patent Application Agent Ref: 65771, incorporated herein by reference in its entirety. In some embodiments, the external sensor unit, i.e. Bio-Medical patch, comprises the following sensors (any possible combination):

a. 3 Dimensional accelerometer sensor optionally to pick up body vibrations of frequencies less than 100 Hz b. Microphone (magnetic or piezoelectric) optionally to pick up audio waves of frequencies from 100 Hz to 5 KHz c. Ultrasound piezoelectric sensor optionally to produce and detect ultrasound signals at 4 MHz. Optionally ultrasound waves will be use to locate the driller tip position and/or assess the distance to the patch and/or to assess cracks and/or fractions with the bone itself, as potentially signal reflection is much difference at bone which is untouched or a bone with a hole in it d. Magnetometers (copper coil) sensor that optionally detect drilling bit metal tip and produce electricity in relations to the tip distance from the patch e. Hall Effect sensor—optionally when the Hall probe is held so that the magnetic field lines are passing at right angles through the sensor of the probe, the meter gives a reading of the value of magnetic flux density (B). Potentially a current is passed through the crystal which, when placed in a magnetic field has a "Hall effect" voltage developed across it.

f. Pickup coils (at numerous variations of installations around the drilled area) optionally to pickup electricity induced from the drilling tip, which is charged with voltage g. Resistance sensor to optionally measure conductivity between driller tip to the patch, through measuring the current run inside the human tissues h. Thermal sensor (based on Infra-Red waves read and/or piezoelectric sensor) to optionally read the body temperature in the area of drilling In some embodiments, the signals of the Bio-Medical patch sensors are being sampled, and/or filtered and optionally sent to the controller computer.

In some embodiments the Bio-Medical patch is attached to the body with the aid of either biological glue and/or hydro gel compound potentially ensuring good transfer of signals from the body.

In some embodiments, the Bio-Medical patch is produced in different forms, other than patches, such as for example: Mattress cover to be placed under the patient bed or head throne that will cover patient head during neurological surgery or belly belt to be used in spinal surgery.

In some embodiment the Bio-Medical patch is connected to Controller computer, optionally connected to an automated drilling robot to optionally send acquired signals and/or enhance drilling robot information regarding the progress of the drilling and/or enhance decision making of when to stop the drilling.

In some embodiments the Add-on adaptor and/or the Bio-Medical patch can be produced for single use only and/or for a multiple uses, optionally in surgeries with the ability to be sterilized before use.

In some embodiments, the controller computer comprises a user interface optionally to control all drilling parameters before the surgery start, and/or display the progress of the drilling during the surgery and/or review option to track all surgeon performance to allow later review.

Potential advantages of the invention may include the following:

a. The invention may prevent harming tissues other than the bone by stopping the driller on time (drilling only the bone itself)

b. The bone drilling controlling device of the invention might be quicker to use by surgeons and as overall performance, shortening the Orthopedics/Neurologic surgery time. Further, the device of the invention might be safer to the patients and/or reduce risks of being harmed by driller tip penetration after reaching bone cortical layer.

c. The bone drilling controlling device of the invention may reduce patients recovery time after surgery.

d. The approach of having an add-on adaptor that is attached to currently available drillers and drilling bit potentially allows easy adoption of the tool without the need to reeducate the surgeons and way of working This invention is referring to all and any bone (such as scull, spine bones, teeth and/or any other bones) drilling and/or cutting/sawing procedures being done on humans and/or animals perfumed manually or semi-automated/full-automated system.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System for Monitoring and Modifying the Operation of Surgical Bone Tools Reference is now made to FIG. 1, presenting an exemplary high level overview of a system comprising an adaptor for use with a surgical tool, a sensor unit and a control circuit, according to some embodiments of the invention.

According to some exemplary embodiments, adaptor 100 is provided with a surgical tool 120, coupling it to the operating bit 140. In some embodiments, adaptor 100 comprises a mechanical interface for controlling the power transmission from tool 120 motor to bit 140. In some embodiments, controlling includes transmitting the forces generated by tool 120 motor to the operating bit 140, until receiving a signal to cutoff.

According to the exemplary embodiment presented in FIG. 1, a signal to cutoff the power transmission to bit 140 by adaptor 100, is provided by control circuitry 180. In some embodiments, control circuitry 180 decides to send a signal to cutoff based on sensory data provided by sensor unit 160, having at least one sensor.

Although control circuitry 180 is presented in FIG. 1 in the form of a personal computer, it should be noted that it could also be provided alternatively or additionally, according to some embodiments, as embedded within adaptor 100.

Although sensor unit 160 is presented in FIG. 1 in the form of a separate unit, it should be noted that it could also be provided alternatively or additionally, according to some embodiments, as embedded within adaptor 100.

Exemplary Adaptor in Use with a Surgical Drill

Figure 2:
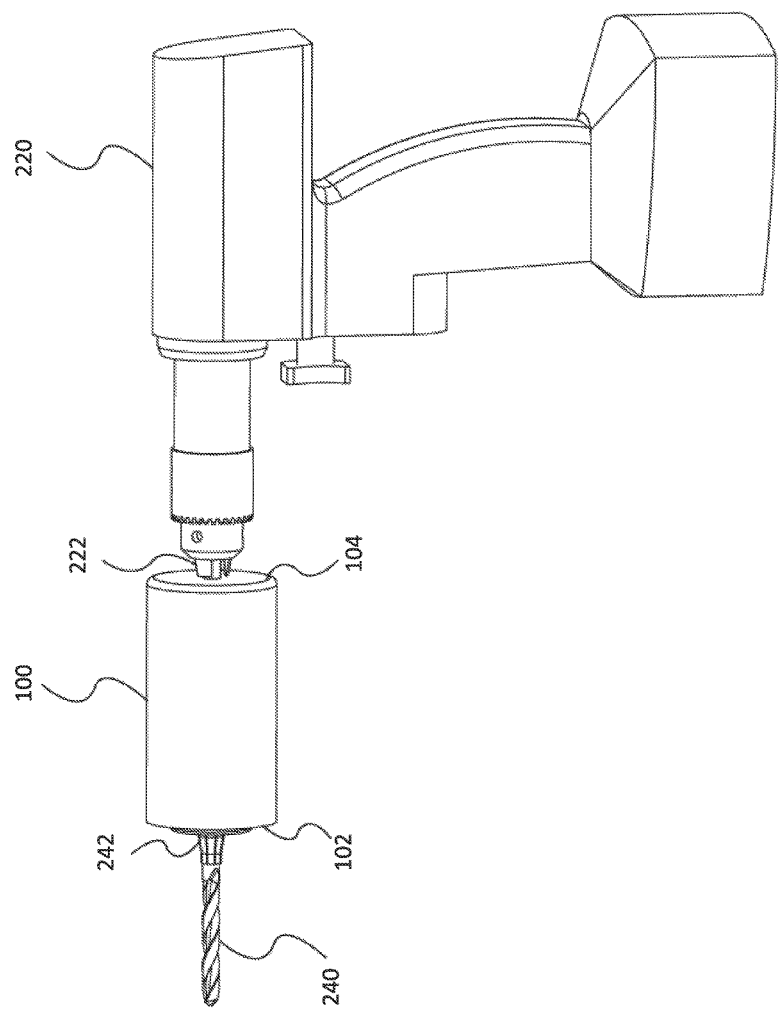
FIG. 2 is an example of an adaptor being in use with a surgical drill, according to some embodiments of the invention.

Reference is now made to FIG. 2, presenting an example of an adaptor 100 being used with a surgical drill. in accordance with some embodiments of the invention.

In some embodiments, adaptor 100 comprises a proximal end 102 for connecting with the drill bit 240, and a distal end 104 for connecting with the surgical drill 220.

In some embodiments, proximal end 102 comprises chuck 242. In some embodiments, chuck 242 comprises an adjustable aperture constricted to fit and clench a drill bit. In some embodiments, proximal end 102 is manufactured being connected to drill bit 240, optionally, a plurality of adaptor is provided having a range of drill bit sizes and shapes.

In some embodiments, the adaptor comprises a shaft sized and shaped to fit with the drill existing chuck 222. Alternatively, adaptor 100 comprises in its distal portion a bore sized and shaped to accommodate the driller's main shaft.

In some embodiments, adaptor 100 is provided having a longitudinal axis dimension of about 30-50 mm, optionally 40 mm. In some embodiments, adaptor 100 is provided having a diameter of about 20-40 mm, optionally 30 mm.

Exemplary Adaptor Specifications

Figure 3:
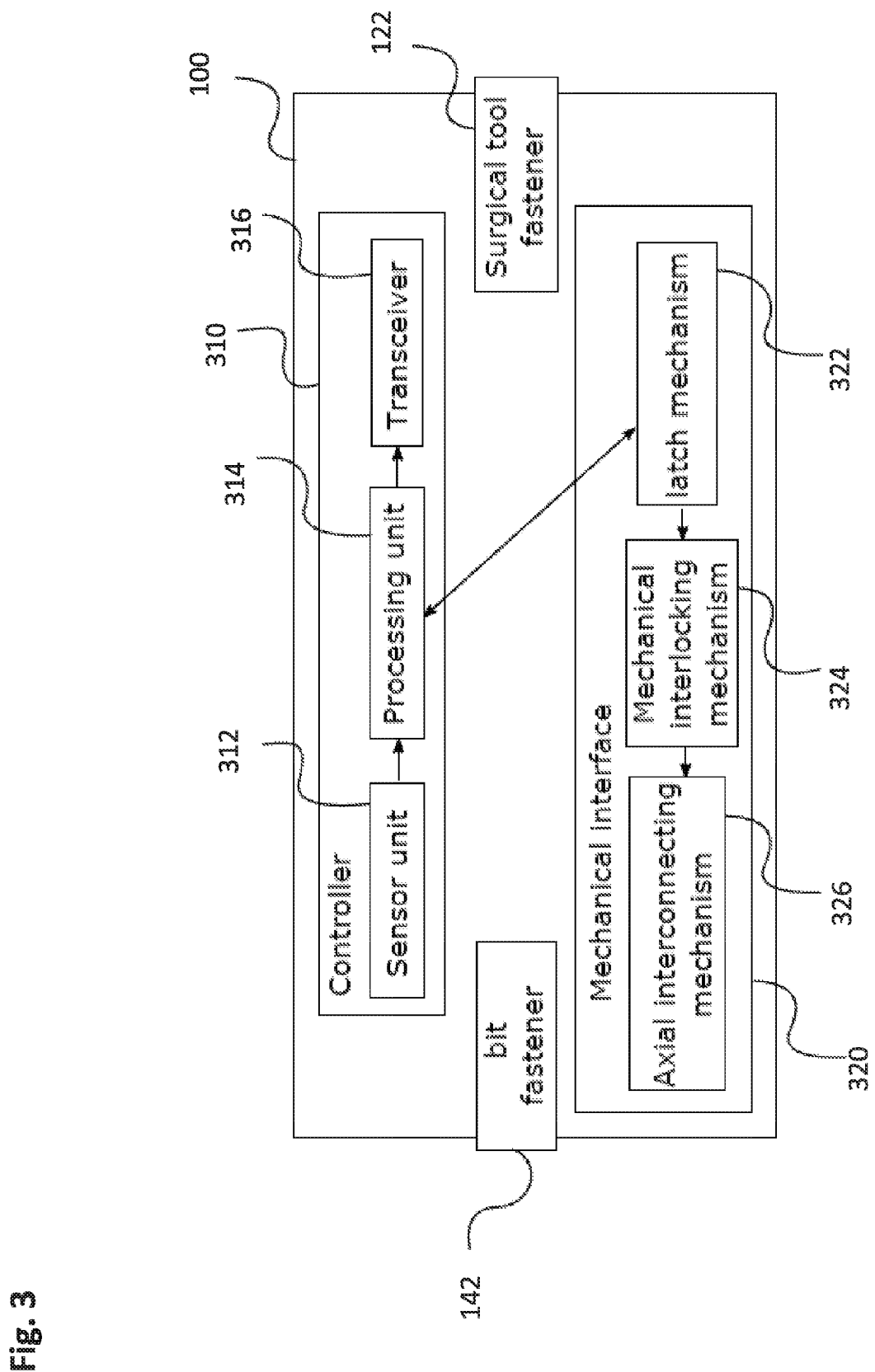
FIG. 3 is a block diagram of exemplary adaptor specifications, according to some embodiments of the invention.

Reference is now made to FIG. 3, presenting a block diagram of exemplary adaptor specifications, according to some embodiments of the invention.

In some embodiments, adaptor 100 is provided for mediating force transmission between the surgical tool and its operating tip. In some embodiments, the adaptor is coupled to the tool by having a bit fastener 142 in its proximal end 102, and a tool fastener 122 in its distal end 104. In some embodiments, force transmission is conducted through the mediating adaptor 100 through mechanical interface 320. In some embodiments, the force transmission is modulated by instructions provided by control circuit 310 to mechanical interface 320.

In an exemplary embodiment of the invention, adaptor 100 provides transmission of radial forces through a mechanical interlocking mechanism 324, for example a clutch, as will be further exemplified below. Alternatively or additionally, adaptor 100 provides transmission of axial forces through an axial interconnecting mechanism 326, for example a stopping spacer. In some embodiments, mechanical engagement of the components comprised in mechanism 324, and/or mechanism 326, leads to force transmission while mechanical disengagement leads to a cutoff of the force transmission.

In some embodiments, a latch mechanism 322 is provided to secure the engaged configuration of mechanical interlocking mechanism 324 and/or axial interconnecting mechanism 326. In some embodiments, latch mechanism 322 includes a magnetic latch solenoid, as will be further described below.

In an exemplary embodiment of the invention, adaptor 100 comprises control circuitry 310. In some embodiments, control circuit 310 comprises sensor unit 312, having at least one sensor. Optionally, sensor unit 312 comprises sensors directed to detecting mechanical aspects of the surgical tool itself.

In some embodiments, control circuit 310 comprises a processing unit 314. In some embodiments, sensory data deriving from sensor unit 312 is transmitted to processing unit 314. In some embodiments, processing unit 314 comprises instructions for analyzing the sensory data, optionally determining a modifying event based on the sensory analysis. In some embodiments, upon determining a modifying event, processing unit 314 provides a signal to latch mechanism 322 to disengage mechanism 324, and/or mechanism 326.

Alternatively or additionally, a modifying event is determined based on data provided from an external source through communication means 316, such as a transceiver, optionally wirelessly. In some embodiments, external data includes a database of bone related information, optionally, containing information with regards to bone parameters. In some embodiments the parameters pertain to bone composition. Alternatively or additionally, parameters pertain to bone size. Alternatively or additionally, parameters pertain to bone stiffness. Alternatively or additionally, parameters pertain to age related bone characteristics.

In some embodiments, the transceiver collects data transmitted from an external sensor unit.

In an exemplary embodiment of the invention, said controller comprises a learning memory module for storing therein feedback information of the bone penetration process. Alternatively or additionally, the feedback comprises sensory data provided by the sensor unit. Alternatively or additionally, the feedback comprises sensory data which has been analyzed by the processor. Alternatively or additionally, the feedback comprises sensory data which has been correlated with a database containing bone parameters data. Alternatively or additionally, the feedback comprises sensory data which has been correlated with a database containing patient related data.

Exemplary Processes of Determining Interaction Cessation

Figure 4B:
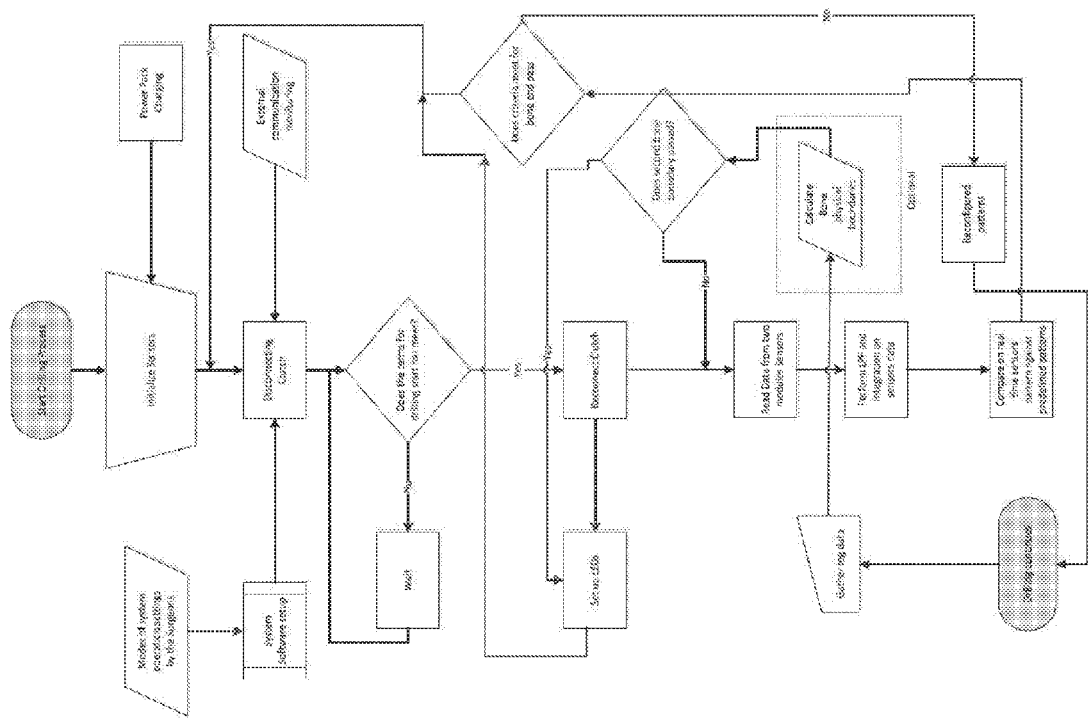

Reference is now made to FIGS. 4A-B, presenting flow charts of exemplary processes of determining a stopping event, or deciding interaction cessation, according to some embodiments of the invention.

According to some exemplary embodiments, the process begins with assembling the adaptor in its distal end to a bone surgical tool, such as a drill or a saw 401. In some embodiments, assembling is conducted using the existing fasteners of the tool, such as through the tool's chuck. In some embodiments, assembling continues by assembling the adaptor in its proximal end to the tool's operating bit 402. Alternatively or additionally, the adaptor may be provided preassembled with the bit in its manufacturing process.

In some embodiments, once the adaptor is assembled and coupled between the tool and the tool's bit, one may operate the tool 403. In some embodiments, operating the tool is conducted as a test, without contacting the patient, optionally to confirm communication with a control unit 410. Potentially, operating the tool in the air without interacting it with the patient provides a baseline for the sensors detecting mechanical aspect of the tool.

In some embodiments, the tool is operated to interact with a patient's bone 404. It should be noted that the term bone as used herein may refer to any of skull, spine, skeleton, teeth and cartilage.

In some embodiments, tool's operation is accompanied by sensing parameters relating to the drilling mechanical operation and/or impact on the bone and/or patient's body 405.

In some embodiments, a modifying event, such as stopping force transmission to the bit, is decided in 406 based on the sensory data received in 405. Alternatively or additionally, drilling is conducted automatically according to a predetermined protocol. According to some embodiments of the invention, a modifying event results from detecting a desirable penetration has occurred. In some embodiments, the detection indicates cortical bone penetration. Alternatively or additionally, the detection indicates cortical bone breakthrough. Alternatively or additionally, the detection indicates identification of trabecular bone penetration. Alternatively or additionally, the detection indicates identification of a predetermined depth range.

According to an exemplary embodiment of the invention, once a modifying event is determined in 406, a signal is transmitted to release the latch mechanism 407.

Alternatively or additionally, an alert is provided. In some embodiments, the alert is a visual notification. Alternatively or additionally, the alert is an audio notification. Alternatively or additionally, the alert is vibratory.

In some embodiments, releasing latch mechanism in 407 results in disengaging the radial interlocking mechanism 420, cutting off transmission of radial forces, optionally resulting from the tool's motor, and/or releasing the axial locking mechanism 430, cutting off transmission of axial forces to the tool bit, optionally resulting from the tool's operator.

Exemplary Override Circuit Algorithm

According to an exemplary embodiment of the invention, a surgical tool is provided with an override circuit having instructions to modify the operation of the tool regardless of the instructions received by the standard operation route.

In some embodiment, the override circuit is coupled to the surgical tool using the adaptor as described herein. In some embodiments, the override circuit comprises a processor, optionally having instructions to analyze input data to provide override operation instructions. Alternatively or additionally, the override circuit comprises a receiver for receiving operation instructions from an external microprocessor. Optionally, the receiver is a wireless receiver. In some embodiments, the override circuit comprises at least one sensor. Alternatively or additionally, the override circuit receives sensory data through the receiver. Alternatively or additionally, the override circuit receives sensory data which has been further analyzed by an external processor.

Figure 5:
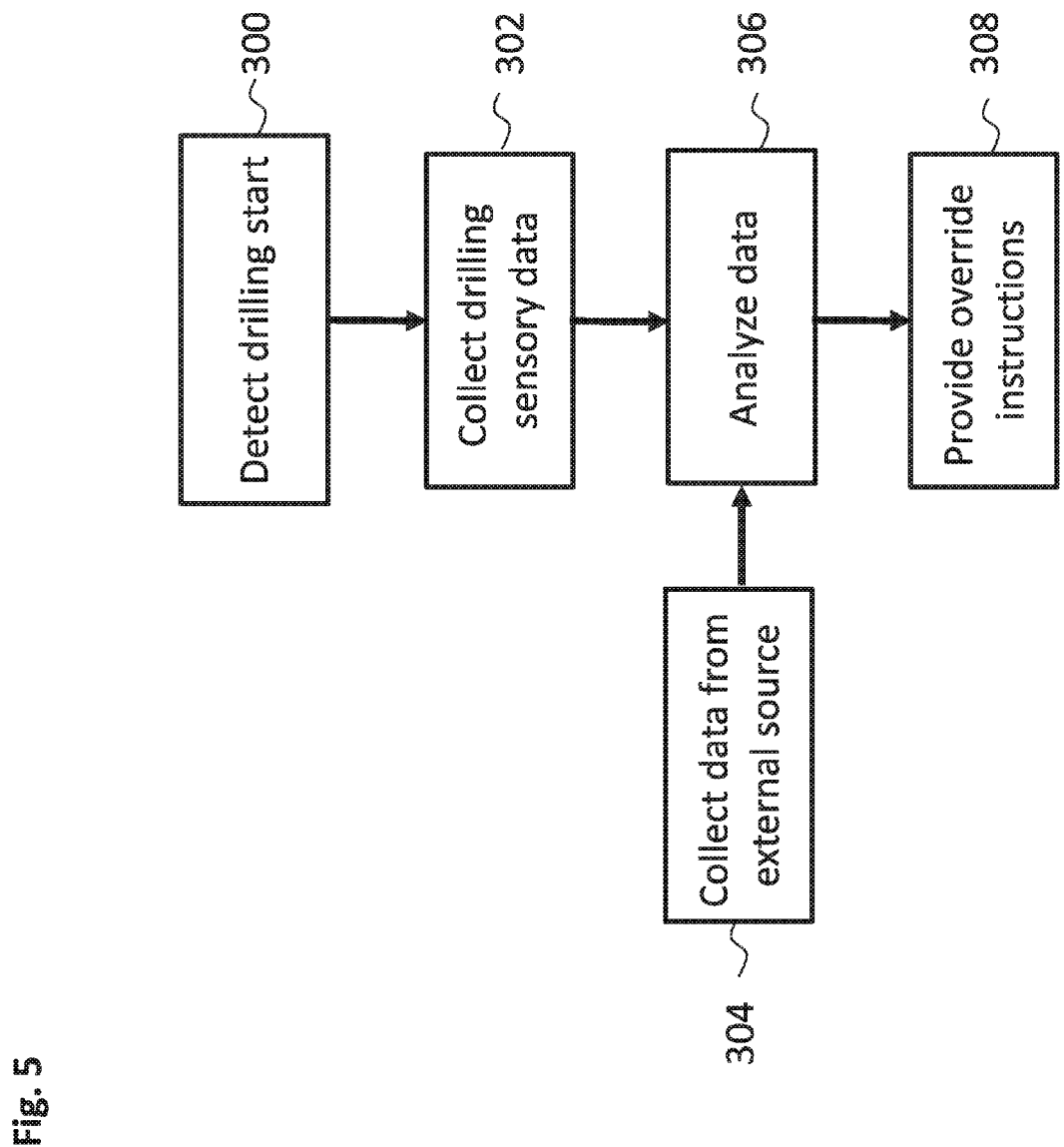
FIG. 5 is a general flow chart of an exemplary override circuit algorithm, according to some embodiments of the invention.

Reference is now made to FIG. 5, presenting a general flow chart of an exemplary override circuit algorithm as used in a drill, according to some embodiments of the invention.

In some embodiments, the algorithm is executed first by detecting drilling has started 300. In some embodiments, detecting drilling has started leads to the turn on of sensory units. According to an exemplary embodiment, sensors are directed to sensing aspects relating to the drilling process itself. Optionally, sensors are selected from the group consisting of torque sensor, pushing/pulling force sensor, radial velocity sensor, drill battery power consumed sensor, three-dimensional Accelerometer sensor, three-dimensional tilt sensor and any combination thereof. According to an exemplary embodiment, once interaction start has been detected, collecting sensory data 302 and 304 is executed.

In some embodiments, collected sensory data is related to mechanical parameters of the drilling process. Alternatively or additionally, collected sensory data is related to physiological parameters of the patient. Alternatively or additionally, sensory data is related to physical properties of the surgery's environment, such as, in a non-limiting example, the temperature or the room, humidity and the like. In some embodiments, collecting sensory data is performed by sensors embedded within the override circuit itself. Alternatively or additionally, sensory data is collected by sensors positioned externally to the override circuit, and optionally transmitted to the override circuit, optionally after being analyzed.

According to some embodiments, once sensory data is collected, analyzing the data is executed 306. In some embodiments, data is analyzed by a microprocessor embedded in the override circuit. Alternatively or additionally, data is analyzed by a microprocessor located externally to the override circuit. In some embodiments the external microprocessor is a server. Alternatively or additionally, and in a non-limiting example, the external microprocessor is in the form of a personal computer, a tablet, a smartphone and the like.

In some embodiments, a graphical user interface (GUI) is provided, optionally for allowing a user to monitor the analysis process. Alternatively or additionally, GUI is provided for a user to manually provide instructions.

According to some embodiments, when sensory data has been analyzed, providing override instructions is executed 308. In some embodiments, override instructions cause the surgical tool to stop the bone penetration. Alternatively or additionally, override instructions cause the cutoff of radial forces from the tool's motor to the tool's operating tip. Alternatively or additionally, override instructions cause the cutoff of axial forces from the tool's motor to the tool's operating tip.

Exemplary Adaptor Configuration

Figures 6A, 6B:
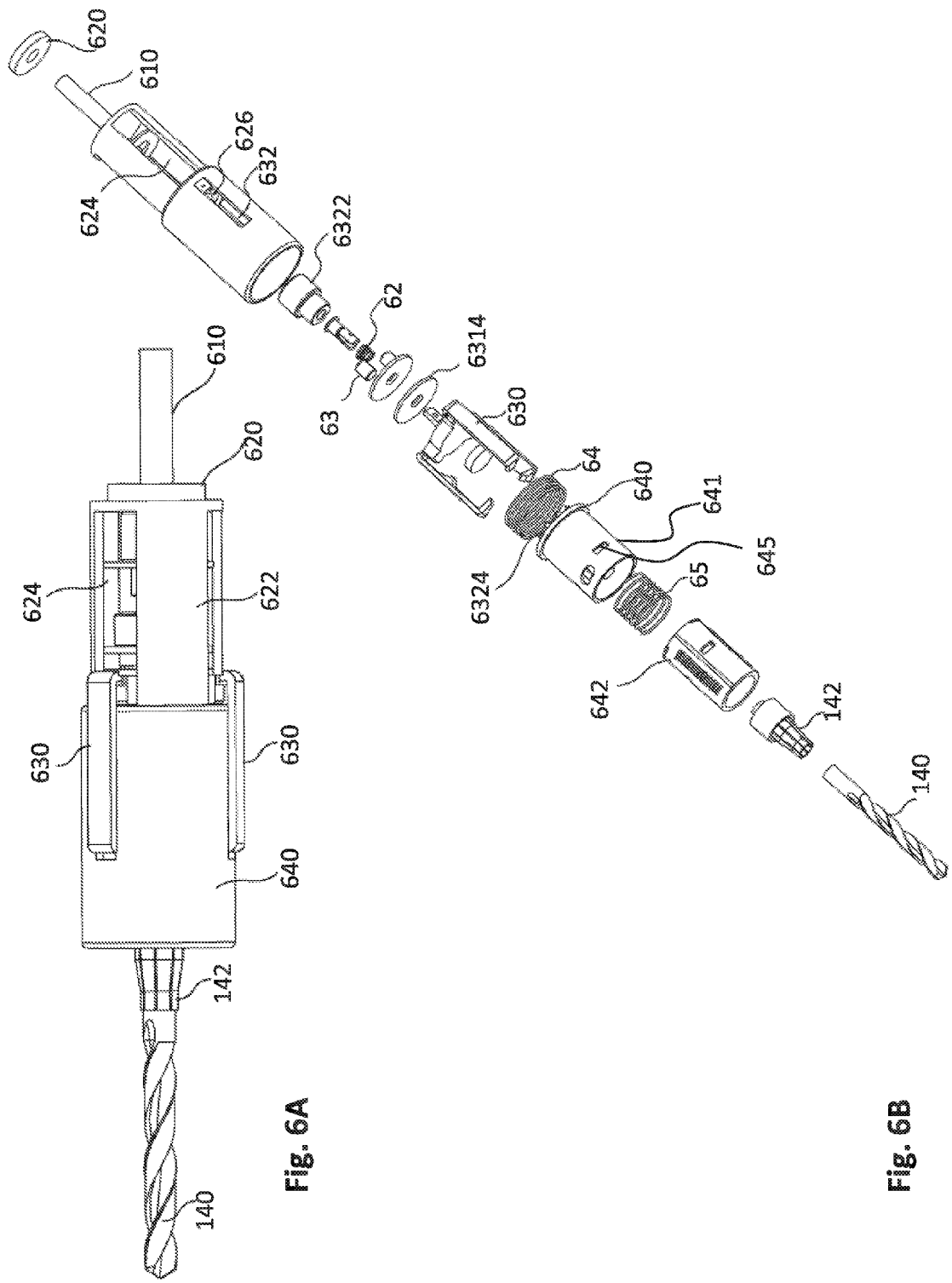

Reference is now made to FIGS. 6A-B, illustrating schematic views of an exemplary adaptor configuration, according to some embodiments of the invention.

Reference is now made to FIG. 6A, illustrating a schematic side view of the exemplary adaptor. In some embodiments, adaptor 100 is provided having a chuck fastener 142 in its proximal end 102, for accommodating a tool bit 140. In some embodiments, adaptor 100 is provided with a fastener 610, sized and shaped to fit into the tool's chuck, as if it were the bit. In some embodiments, fastener 610 is shaped as a shaft. In some embodiments, shaft 610 transmits forces generated in the tool's motor through the mechanical interface provided in adaptor 100, all the way to bit 140, optionally without changing the force power. Optionally, shaft 610 is provided with bearings 620.

In some embodiments, shaft housing 622 is provided for containing the adaptor's latch mechanism. In some embodiments, housing 622 comprises at least one aperture 624. In some embodiments, at least one fastener 630 is provided extending through aperture 624 and for mechanically engaging with the radial and/or axial locking mechanism 640.

Reference is now made to FIG. 6B illustrating a schematic explosive view of the exemplary adaptor. The explosive view illustrates the mechanical interlocking interface and latch mechanism, according to some embodiments of the invention. In some embodiments, shaft housing 622 contains a latch mechanism in the form of a magnetic latch solenoid 6322 and spring 62. In some embodiments, magnetic solenoid latch 6322 holds together the engagement of fastener 630 and the compression of spring 64 and spring 65. In some embodiments, the latch mechanism leads to compression of the mechanical interlocking interface members.

In some embodiments, shaft housing 622 further comprises sensor unit 6314. In some embodiments, shaft housing 622 further comprises batteries 63.

In some embodiments, base 640 is provided with an interface 6324 configured to interlock with a matching interface. In some embodiments, matching interface 626 is comprised in shaft housing 622. In some embodiments, interface 6324 and matching interface 626 comprise a plurality of pins and cavities, sized and shaped to interlock. Alternatively or additionally, interfaces 6324 and 626 comprise complementary jutties. Alternatively or additionally, interfaces 6324 and 626 comprise complementary serrated interfaces.

In some embodiments, base 640 is connected to the axial locking mechanism.

In some embodiments, the axial mechanism is provided in the form of at least one outer member 641 fitted over inner member 642, optionally telescopically. In some embodiments, one of members 641 and 642, or both, is cylindrical. In some embodiments, the members are held together with a locking clasp. Alternatively or additionally, the members are held together with a ratchet mechanism, optionally wherein one member, or both, is unidirectional and one member, or both, is elastic. In some embodiments, inner member 642 or outer member 641, or both, comprise ratchet like jutties and/or at least one aperture.

In some embodiments, outer member 641 comprises a slit 645 for engaging with fastener 630, optionally for holding interface 6324 engaged with interface 626 against a resistance, such as spring 64.

Exemplary Mechanical Interface of an Adaptor Configured for a Drill

Figure 7A:
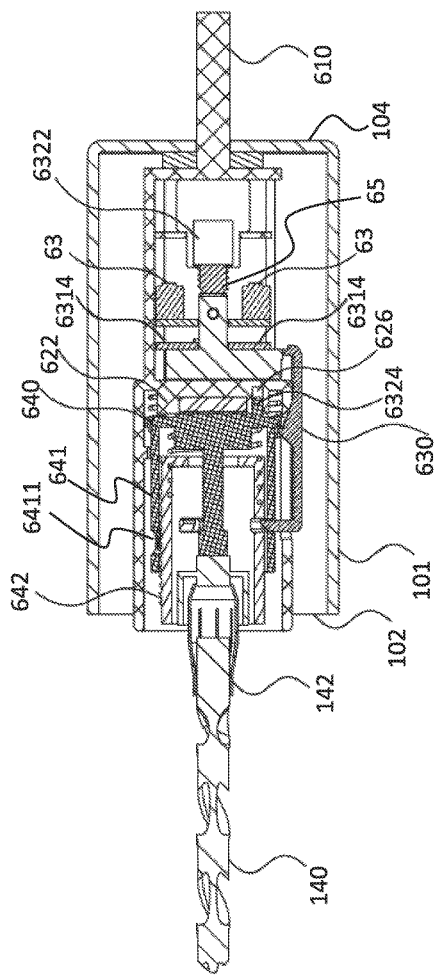
Figure 7B:
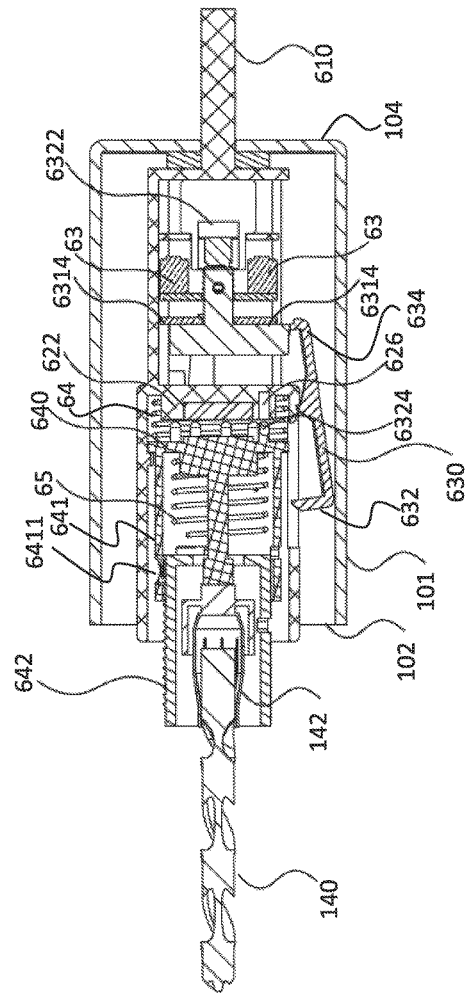

Reference is now made to FIGS. 7A-B, illustrating schematic cross-sectional side views of an exemplary mechanical interface of an adaptor configured for a drill, according to some embodiments of the invention.

Reference is now made to FIG. 7A illustrating an engaged configuration.

According to some embodiments, adaptor 100 is provided with housing 101, having a proximal end 102 and distal end 104. In some embodiments, proximal end 102 comprises a drill chuck 142 for accommodating drill bit 140. In some embodiments, distal end comprises shaft 610 for fitting into the drill chuck.

In some embodiments, shaft 610 is connected to shaft housing 622. In some embodiments, the proximal portion of housing 622 ends with interface 626. In some embodiments, housing 622 contains the latch mechanism, for example magnetic solenoid latch 6322.

In some embodiments, interface 626 is held engaged with interface 6324 against a resistance, optionally in the form of spring 64. In some embodiments, base 640 comprising interface 6324 is held together against interface 626 by fastening shaft housing 622 to outer and inner members 642 and 641, optionally through an outer fastener such as 630. In some embodiments, either interface 6324 or interface 626, or both, are provided with magnets to further promote their mechanical engagement.

Reference is now made to FIG. 7B illustrating a disengaged configuration. In some embodiments, the magnetic latch is disconnected by transmitting current through solenoid, causing the magnetic latch solenoid to change its polarity. In some embodiments, once the latch is disconnected, shaft housing 622 is shifted axially in to the direction of distal portion 104. In some embodiments, the shift of shaft housing 622 mechanically pulls fastener 630. In some embodiments, fastener 630 comprises hinge 634, configured to tilt when fastener 630 is pulled. Once fastener 630 is tilted, locking member 632 is removed from its engagement with inner and outer members 641 and 642, leading to their release towards proximal end 104, by the released compression of springs 64 and 65, causing the axial force transmission cutoff. In some embodiments, releasing springs 64 and 65 together with the pulling of housing 622 leads to the mechanical disengagement of interfaces 6324 and 626.

In some embodiments, after fastener 630 is released, inner member 642 translates axially to outer member 641. In some embodiments, the released state of members 642 and 641 is locked, potentially blocking further axial force administration to the drill bit.

Reference is now made to FIGS. 8A-B, illustrating schematic cross-sectional side views of an exemplary use of an adaptor in a drill, according to some embodiments of the invention, wherein FIG. 8A illustrates an engaged configuration and FIG. 8B illustrates a disengaged configuration, and in which like reference numerals designate like parts as in FIGS. 7A-B.

In FIG. 8A, illustrated is the drill bit 140 penetration into bone 800, exemplifying the engaged configuration of adaptor 100, and the inner position of inner member 642.

In FIG. 8B, illustrated is the incipient breakthrough of drill bit 140 through the cortical bone tissue 801, exemplifying the disengaged configuration of adaptor 100, and the external position of inner member 642, potentially blocking further axial penetration of bit 140.

Exemplary Engaged and Disengaged Mechanical Interlocking Interface

Reference is now made to FIGS. 9A-C, illustrating schematic views of an exemplary mechanical interlocking interface having an engaged configuration, according to some embodiments of the invention, wherein FIG. 9A illustrates a perspective view, FIG. 9B illustrates a side view and FIG.

9C illustrates a cross-sectional side view, according to line l in FIG. 9B, and in which like reference numerals designate like parts.

According to exemplary embodiments of the invention, fastener 630 interconnects the magnetic solenoid latch 6322 together with the inner and outer members 641 and 642. This connection results in the engagement of the mechanical interlocking interface 6324 through clasp 636, and alternatively or additionally, the engagement of inner and outer members 641 and 642 through clasp 632.

Reference is also made to FIGS. 10A-C, illustrating schematic views of an exemplary mechanical interlocking interface having a disengaged configuration, according to some embodiments of the invention, wherein FIG. 10A illustrates a perspective view, FIG. 10B illustrates a side view and FIG. 10C illustrates a cross-sectional side view, according to line L in FIG. 10B and in which like reference numerals designate like parts.

According to exemplary embodiments of the invention, once the magnetic solenoid latch 6322 is activated, optionally by transmitting an electrical current through the solenoid, the changed polarity of magnet 6322 results in the pulling of fastener 630. In some embodiments, fastener 630 is provided with hinge 634 which upon pulling of fastener 630 causes it to tilt. Potentially, tilting of fastener 630 causes it to snap away its locking members 636 and 632, leading to the release of both the radial mechanical interface 6324 and the axial locking mechanism of members 641 and 642.

In some embodiments, the released position of members 641 and 642 is maintained by a securing mechanism 644. In some embodiments, the securing mechanism 644 is comprised of a ratchet mechanism, optionally wherein one member, or both, is unidirectional and one member, or both, is elastic.

In some embodiments, manual locking clasp 964 is provided in outer member 641. Manually locking clasp 964 prevents the automatic disengagement of the radial and axial mechanical interfaces of adaptor 100.

Exemplary Embodiment of Mechanical Interlocking Mechanism

Reference is now made to FIGS. 11A-B, illustrating schematic views of another exemplary mechanical interlocking interface, according to some embodiments of the invention, wherein FIG. 11A illustrates a perspective view and FIG. 11B illustrates an explosive view.

According to several embodiments of the invention, adaptor 100 comprises a mechanical interface as illustrated herein in FIGS. 11A-B and FIGS. 12A-B. In some embodiments, the adaptor comprises a chuck 1141 for accommodating an operating bit 1142. In some embodiments, main shaft 1161 is provided in the adaptor's distal end, optionally sized and shaped to fit into the surgical tool bit fastener. In some embodiments, the main shaft 1161 comprises interlocking interface 1126 in its proximal end, configured to mechanically interlock with interface 1124.

In some embodiments, interlocking interfaces 1126 and 1124 are compressed together against a resistance, optionally at least one spring 1133. Exemplified is an embodiment having three springs 1133. In some embodiments, each of springs 1133 is stabilized by an inner member 1132, optionally shaped as a pin. Optionally, inner members 1132 are positioned over a base, such as ring 1140. In some embodiments, springs 1133 are compressed by enclosing outer member 1162 over inner members 1132. Optionally, 1162 is shaped as a canister having accommodating portions 1131 for inner members 1132.

In some embodiments, sensor unit 1114 is embedded within the adaptor, optionally between the chuck 1141 and the interlocking interface of 1126 with 1124.

Figure 12A:
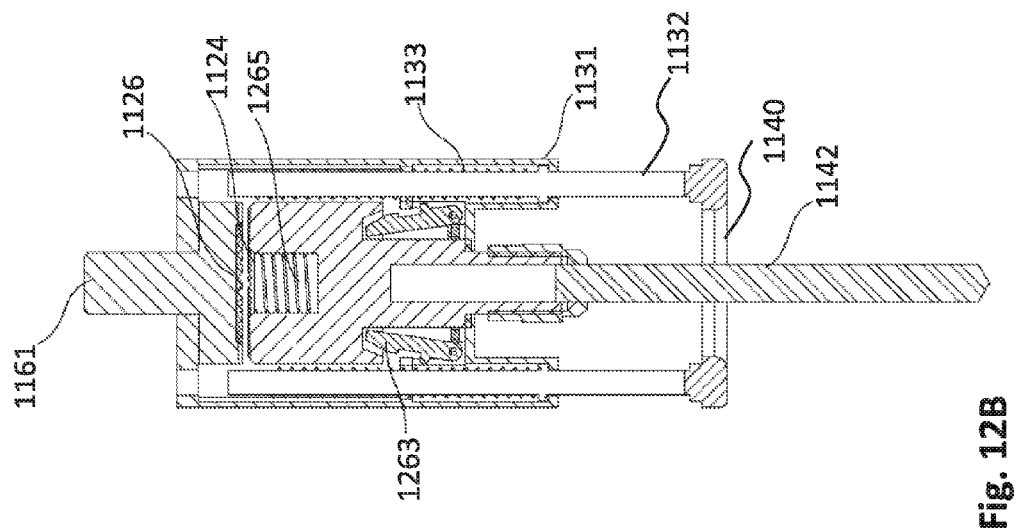
Figure 12B:
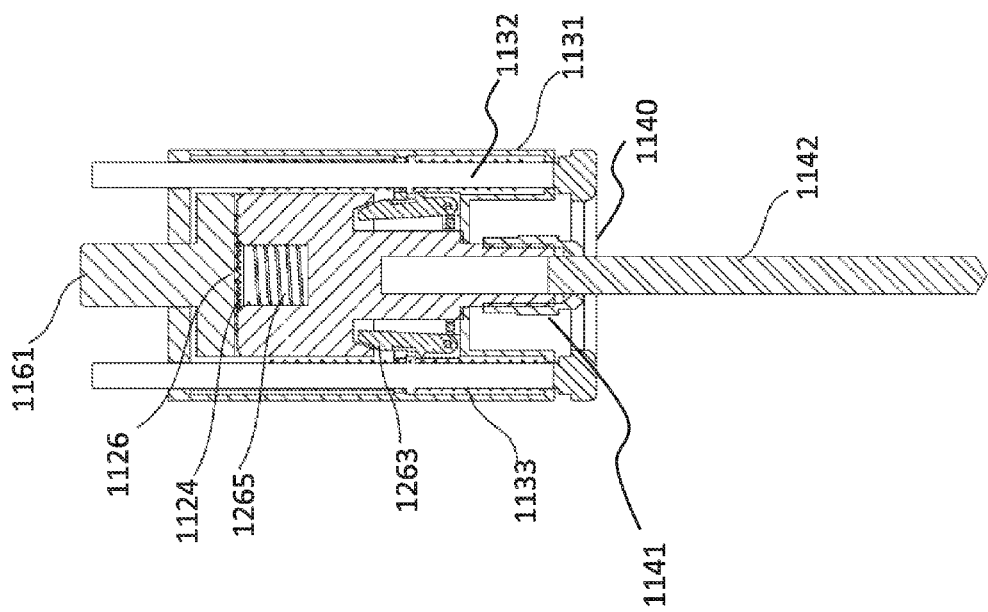

Reference is now made to FIGS. 12A-B, illustrating schematic cross-sectional side views of the exemplary mechanical interlocking interface illustrated in FIGS. 11A-B, according to some embodiments of the invention, wherein FIG. 12A illustrates an engaged configuration and FIG. 12B illustrates a disengaged configuration.

Exemplified in FIGS. 12A-B is at least one clasping member 1263 for locking the relative axial position of inner members 1132 and outer member 1162, according to some embodiments of the invention. Once the magnetic solenoid latch of the adaptor is activated, mechanical interfaces 1124 and 1126 disengage. In some embodiments, activation of the magnetic solenoid leads to release of clasping member 1263, potentially discharging springs 1133 and causing the release of inner members 1132. According to several embodiments, when inner members 1132 are released, base 1140 is pushed away from chuck 1141, resulting in the cutoff of axial forces transmission to the bit 1142.

Exemplary Embodiment of an Adaptor Used with a Surgical Saw

Figure 13:
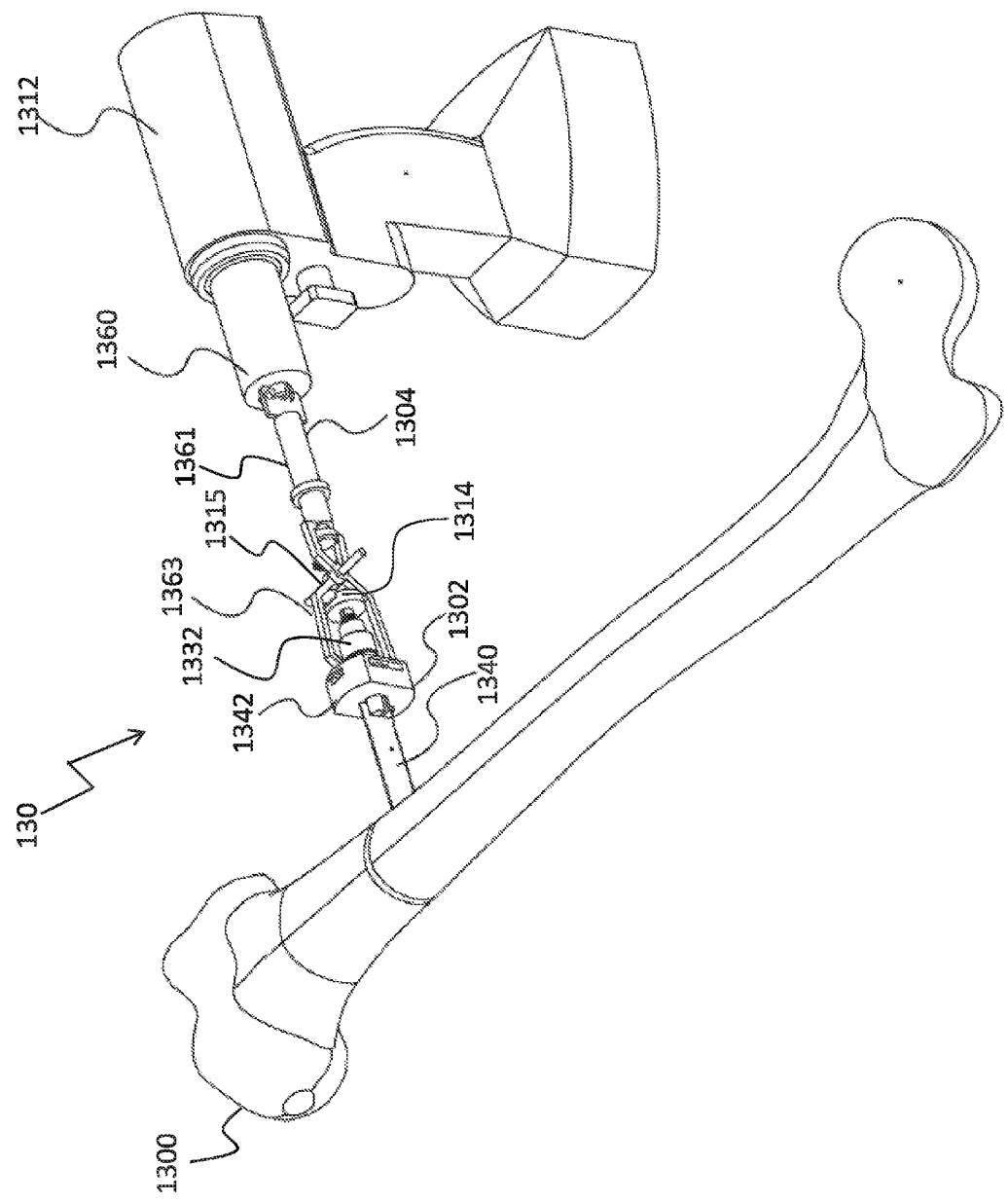
FIG. 13 illustrates an exemplary embodiment of the adaptor for use with a surgical saw, according to some embodiments of the invention.

Reference is now made to FIG. 13, illustrating an exemplary embodiment of the adaptor for use with a surgical saw, according to some embodiments of the invention. In some embodiments, adaptor 130 is configured to be used with a saw, and provided in its distal end 1304 with axle 1361, shaped and sized to fit into the saw chuck 1360 in the saw tool 1312. In some embodiments, adaptor 130 is provided in its proximal end 1302 with saw chuck 1342 for accommodating saw bit 1340 shown here used for cutting bone 1300.

In some embodiments, the mechanical interface of saw adaptor 130 includes at least two arms 1363 interconnecting axle 1361 in the distal end to the saw chuck 1320 in the proximal end. In some embodiments, arms 1363 are provided with pin 1315 inserted perpendicularly to the arms main axis, enabling their potential rotation around the distal-proximal axis, optionally in a scissors-like manner. In some embodiments, the arms 1363 cause saw chuck 1342, and accordingly saw bit 1340, to move back and forth in an axial movement, without force modification, as if the saw bit 1340 was connected to the saw tool chuck 1360. Alternatively, in some embodiments, the clutch mechanism enables transmission and cutoff of vibratory forces. Optionally, vibratory forces include forces in all axis directions and planes, (x/y/z/θ planes).

In some embodiments, latch mechanism 1332, optionally a magnetic solenoid latch, holds the arms in their engaging position, as will be further described below.

In some embodiments, adaptor 130 comprises sensor unit 1314.

Figure 14B:
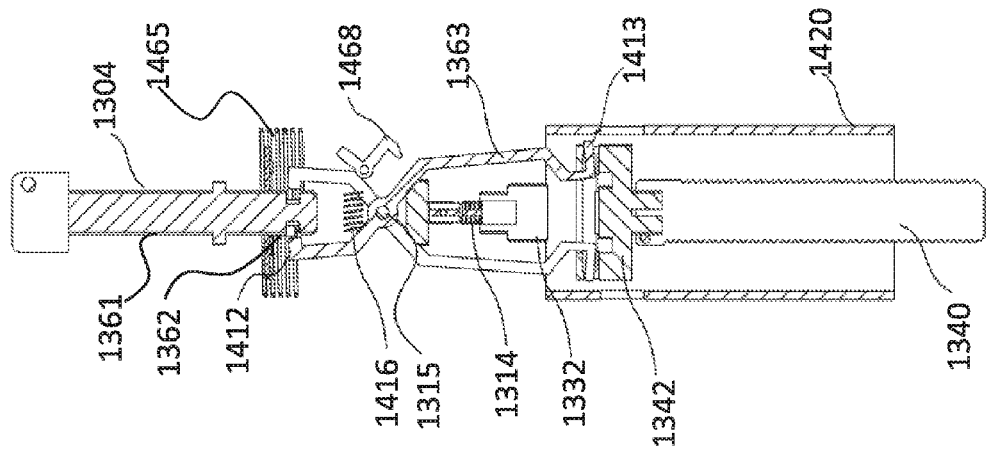
Figure 14A:
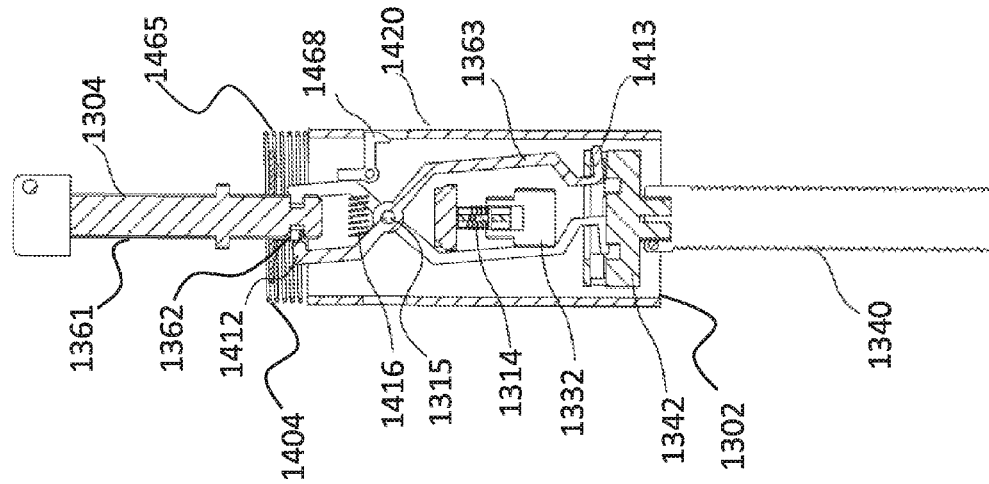

Reference is now made to FIGS. 14A-E, illustrating schematic cross-sectional side views and perspective views of an exemplary mechanical interlocking interface of the adaptor as illustrated in FIG. 13, according to some embodiments of the invention, wherein FIG. 14A illustrates a cross-sectional side view of an engaged configuration, FIG. 14B illustrates a cross-sectional side view of a disengaged configuration, FIG. 14C illustrates a perspective view of an engaged configuration, FIG. 14D illustrates a perspective view of a disengaged configuration and FIG. 14E illustrates an enlargement of the circular inset shown in FIG. 14D.

In some embodiments, arms 1363 comprise interlocking interfaces 1413 and 1412 in its proximal and distal ends, respectively, optionally in the form of clasps 1413 and 1412, for connecting with the saw bit 1342 and the main axis 1361, respectively. In some embodiments, clasps 1412 are mechanically engaged with at least one recess 1362 provided in axis 1361.

In some embodiments, sleeve 1420 holds the arms clasped in the engaged position, optionally by comprising a sleeve arm 1468, optionally being pressed against 1420, or alternatively or additionally, having a clasp and slit locking mechanism. In some embodiments, once latch 1332 changes its polarity, it causes arms 1363 to move away from each other and from the central axis of the adaptor, resulting in the release of sleeve arm 1468, optionally together with the release of spring 1416. As a result, sleeve 1420 is pushed towards the proximal end by the release of spring 1465, and potentially serving as a mechanical stopper for further penetration of the saw bit 1340 into the bone.

An enlarged view of the release mechanism according to the above embodiment is depicted in FIG. 14E, illustrating disengaged arms 1363 and disengaged clasps 1412, further separated by spring 1416.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An adaptor capable of being used with and mounted onto an operational surgical bone-tool and for modifying the operation thereof, said adaptor comprising:
    a housing having a proximal end for mechanically coupling to a chuck of said tool, and a distal end for mechanically coupling to an operating bit of said tool, such that force generated by a motor of said tool and coupled to said proximal end is delivered to said operating bit through said adaptor;
    wherein said distal end comprises a bit fastener including a chuck of said adaptor coupled thereto and extending distally from said distal end of said housing, sized and shaped to connect with said operating bit, and
    wherein said proximal end comprises a surgical tool fastener being a rod coupled thereto and extending proximally from said proximal end of said housing, sized and shaped to connect with said chuck of said tool;
    a clutch, contained in said housing, having an engaged configuration operatively interconnecting said bit fastener with said surgical tool fastener, and a disengaged configuration operatively mechanically disconnecting said operating bit from said surgical tool fastener; and
    a circuitry within said housing which automatically and mechanically disengages said clutch in response to an electric signal, causing a mechanical cutoff of said force delivery;
    a latch mechanism, contained in said housing, having an ON activation state and an OFF activation state, and wherein a transition between said ON and said OFF activation states results in a transition between said engaged configuration and said disengaged configuration of said clutch, respectively, and
    wherein, in response to an electrical signal, said circuitry actuates said latch mechanism to release a spring-loaded stopping spacer, contained in said housing, to translate axially in a distal direction within the housing past said adaptor chuck, such that transmission of axial forces by the adaptor are via said stopping spacer, rather than only via said adaptor chuck and any operating bit therein, thereby interfering with axial advance of said operating bit.

2. The adaptor according to claim 1, wherein said housing is configured to be connected to the chuck of the tool and to the operating bit only by said fasteners and is configured to freely rotate in conjunction with a rotating motion generated by said motor.

3. The adaptor according to claim 1, wherein said housing is stationary, while said fasteners and chuck rotate in conjunction with a rotating motion generated by said motor.

4. The adaptor according to claim 1, wherein said latch mechanism is a magnetic solenoid latch.

5. The adaptor according to claim 1, wherein said clutch comprises at least two members, each member having a first interface with a complementary geometry to at least one second interface of a second member of the at least two members.

6. The adaptor according to claim 5, wherein in said engaged configuration said first and said at least one second interfaces are compressed together against a resistance.

7. The adaptor according to claim 1, wherein said stopping spacer providing a cutoff of an axial force delivered to the bit.

8. The adaptor according to claim 7, wherein said stopping spacer comprises at least one outer member and at least one inner member, at least partially overlapping along a proximal-distal axis of the adaptor.

9. The adaptor according to claim 7, comprising at least one fastener coupling said clutch and said stopping spacer against a resistance.

10. The adaptor according to claim 9, wherein the transition of the latch mechanism translates said at least one fastener away from the proximal-distal axis of the adaptor, thereby releasing said coupling of said at least one fastener.

11. The adaptor according to claim 1, further comprising a battery configured to operate for a duration of a bone surgery.

12. The adaptor according to claim 1, wherein said clutch can be transitioned back from said disengaged configuration to said engaged configuration.

13. The adaptor according to claim 12, wherein said back transition is provided by operating said motor in reverse.

14. The adaptor according to claim 7, wherein said disengaged configuration comprises a canister mechanically obstructing axial movement of the operating bit towards a patient's body.

\* \* \* \* \*